US011701656B2

(12) United States Patent
Cai et al.

(10) Patent No.: US 11,701,656 B2
(45) Date of Patent: Jul. 18, 2023

(54) MULTI-DROPLET CAPTURE

(71) Applicant: The Regents of the University of Michigan, Ann Arbor, MI (US)

(72) Inventors: Dawen Cai, Ann Arbor, MI (US); Daniel Nunez, Ann Arbor, MI (US); Katsuo Kurabayashi, Ann Arbor, MI (US); Meng-Ting Chung, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 392 days.

(21) Appl. No.: 16/957,338

(22) PCT Filed: Jan. 2, 2019

(86) PCT No.: PCT/US2019/012039
§ 371 (c)(1),
(2) Date: Jun. 23, 2020

(87) PCT Pub. No.: WO2019/136058
PCT Pub. Date: Jul. 11, 2019

(65) Prior Publication Data
US 2020/0330991 A1 Oct. 22, 2020

Related U.S. Application Data

(60) Provisional application No. 62/612,755, filed on Jan. 2, 2018.

(51) Int. Cl.
*B01L 3/00* (2006.01)
*C12Q 1/6874* (2018.01)
*G01N 1/28* (2006.01)

(52) U.S. Cl.
CPC ... *B01L 3/502761* (2013.01); *B01L 3/502715* (2013.01); *B01L 3/502792* (2013.01);
(Continued)

(58) Field of Classification Search
None
See application file for complete search history.

(56) References Cited

U.S. PATENT DOCUMENTS 5,695,934 A 12/1997 Brenner
5,714,330 A 2/1998 Brenner et al.
(Continued)

FOREIGN PATENT DOCUMENTS

JP 2017-514487 6/2007
WO WO 00/018957 4/2000
(Continued)

OTHER PUBLICATIONS

International Search Report and Written Opinion for PCT/US19/12039, dated Mar. 21, 2019. 11 pages.
(Continued)

*Primary Examiner* — J. Christopher Ball
(74) *Attorney, Agent, or Firm* — Casimir Jones, S.C.; Jason R. Bond

(57) ABSTRACT

Provided herein are systems, methods, and articles of manufacture for collecting and merging two different size droplets using a substrate comprising a plurality of trapping sites. In certain embodiments, provided herein are systems composed of a plurality of larger droplets and smaller droplets and a substrate comprising a plurality of trapping sites where each trapping site is configured to trap only one of the larger droplets and only one of the smaller droplets when the larger droplet is already present at the trapping site. In particular embodiments, the larger and/or smaller droplets are sorted prior to being contacted with the substrate to ensure they contain the desired component (e.g., cell or barcoded bead). In other embodiments, each trapping site is composed of one or multiple fluidically linked capture wells. In some embodi-
(Continued)

ments, collected larger and smaller droplets are merged (e.g., via a demulsifier or electricity).

20 Claims, 21 Drawing Sheets

(52) U.S. Cl.
CPC .............. *C12Q 1/6874* (2013.01); *G01N 1/28* (2013.01); *B01L 2200/0673* (2013.01); *B01L 2200/16* (2013.01); *B01L 2300/0645* (2013.01); *B01L 2300/0654* (2013.01); *B01L 2300/0819* (2013.01); *B01L 2300/12* (2013.01); *B01L 2400/0415* (2013.01)

(56) References Cited

U.S. PATENT DOCUMENTS

| | | |
|---|---|---|
| 5,750,341 A | 5/1998 | Macevicz |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,833,246 B2 | 12/2004 | Balasubramanian |
| 8,481,292 B2 | 7/2013 | Casbon et al. |
| 8,835,358 B2 | 9/2014 | Fodor et al. |
| 8,865,470 B2 | 10/2014 | Yan et al. |
| 2005/0130173 A1 | 6/2005 | Leamon et al. |
| 2007/0020640 A1 | 1/2007 | McCloskey et al. |
| 2007/0195127 A1 | 8/2007 | Ahn et al. |
| 2009/0068170 A1 | 3/2009 | Weitz et al. |
| 2012/0010091 A1 | 1/2012 | Linnarson |

FOREIGN PATENT DOCUMENTS

| | | |
|---|---|---|
| WO | WO 2006/084132 | 8/2006 |
| WO | WO 2014/201272 | 12/2014 |
| WO | WO 2015/157567 | 10/2015 |
| WO | WO 2015/168161 | 11/2015 |
| WO | WO 2016/179291 | 11/2016 |
| WO | WO 2016/193758 | 12/2016 |
| WO | WO 2017/165791 | 9/2017 |

OTHER PUBLICATIONS

Abate et al., Beating Poisson encapsulation statistics using close-packed ordering. Lab Chip. Sep. 21, 2009;9(18):2628-31.
Adessi et al., Solid phase DNA amplification: characterisation of primer attachment and amplification mechanisms. Nucleic Acids Res. Oct. 15, 2000;28(20):E87. 8 pages.
Anna et al., Formation of dispersions using "flow focusing" in microchannels. Appl. Phys. Lett., 2003, 82, 364-366.
Baret et al., Fluorescence-activated droplet sorting (FADS): efficient microfluidic cell sorting based on enzymatic activity. Lab Chip. Jul. 7, 2009;9(13):1850-8.
Baroud et al., Dynamics of microfluidic droplets. Lab Chip. Aug. 21, 2010;10(16):2032-45.
Bennett et al., Toward the 1,000 dollars human genome. Pharmacogenomics. Jun. 2005;6(4):373-82.
Birren et al., Genome Analysis: Analyzing DNA. 1, Cold Spring Harbor, N.Y. 1997. TOC only. 12 pages.
Bontoux et al., Integrating whole transcriptome assays on a lab-on-a-chip for single cell gene profiling. Lab Chip. Mar. 2008;8(3):443-50.
Brenner et al., Gene expression analysis by massively parallel signature sequencing (MPSS) on microbead arrays. Nat Biotechnol. Jun. 2000;18(6):630-4.
Cao et al., Droplet sorting based on the No. of encapsulated particles using a solenoid valve. Lab Chip. Jan. 7, 2013;13(1):171-8.

Chung et al., Deterministic droplet-based co-encapsulation and pairing of microparticles via active sorting and downstream merging. Lab Chip. Oct. 25, 2017; 17(21):3664-3671.
Chung et al., Sort'N merge: A deterministic microfluidic platform for co-encapsulating distinct particles in microdroplets. Proceedings of the IEEE International Conference on Micro Electro Mechanical Systems (MEMS). 2018. 4 pages.
Collins et al., The Poisson distribution and beyond: methods for microfluidic droplet production and single cell encapsulation. Lab Chip. Sep. 7, 2015;15(17):3439-59.
Craig et al., Identification of genetic variants using bar-coded multiplexed sequencing. Nat Methods. Oct. 2008;5(10):887-93.
Edd et al., Controlled encapsulation of single-cells into monodisperse picolitre drops. Lab Chip. Aug. 2008;8(8):1262-4.
Esumi et al., Method for single-cell microarray analysis and application to gene-expression profiling of GABAergic neuron progenitors. Neurosci Res. Apr. 2008;60(4):439-51.
Fradet et al., Combining rails and anchors with laser forcing for selective manipulation within 2D droplet arrays. Lab Chip. Dec. 21, 2011;11(24):4228-34.
Hollas et al., A stochastic approach to count RNA molecules using DNA sequencing methods. Lecture Notes in Computer Science vol. 2812, 2003, pp. 55-62.
Hong et al., Single-cell level co-culture platform for intercellular communication. Integr Biol (Camb). Apr. 2012;4(4):374-80.
Hu et al., Efficient cell pairing in droplets using dual-color sorting. Lab Chip. Oct. 21, 2015;15(20):3989-93.
Hug et al., Measurement of the number of molecules of a single mRNA species in a complex mRNA preparation. J Theor Biol. Apr. 21, 2003;221(4):615-24.
Klein et al., Droplet barcoding for single-cell transcriptomics applied to embryonic stem cells. Cell. May 21, 2015;161(5):1187-1201.
Konry et al., Innovative Tools and Technology for Analysis of Single Cells and Cell-Cell Interaction. Annu Rev Biomed Eng. Jul. 11, 2016;18:259-84.
Konry et al., Live single cell functional phenotyping in droplet nano-liter reactors. Sci Rep. Nov. 11, 2013;3:3179.
Labanieh et al., Floating Droplet Array: An Ultrahigh-Throughput Device for Droplet Trapping, Real-time Analysis and Recovery. Micromachines (Basel). Oct. 2015;6(10):1469-1482.
Lagus et al., High-throughput co-encapsulation of self-ordered cell trains: cell pair interactions in microdroplets. RSC Adv., Mar. 2013, 20512-20522.
Lee et al., On-demand, parallel droplet merging method with non-contact droplet pairing in droplet-based microfluidics. Microfluidics and Nanofluidics, 2016. 20(1). 1-9.
Lee et al., Synchronized reinjection and coalescence of droplets in microfluidics. Lab Chip. Feb. 7, 2014;14(3):509-13.
MacLean et al., Application of 'next-generation' sequencing technologies to microbial genetics. Nat Rev Microbiol. Apr. 2009;7(4):287-96.
Macosko et al., Highly Parallel Genome-wide Expression Profiling of Individual Cells Using Nanoliter Droplets. Cell. May 21, 2015;161(5):1202-1214.
Margulies et al., Genome sequencing in microfabricated high-density picolitre reactors. Nature. Sep. 15, 2005;437(7057):376-80.
Mazutis et al., Single-cell analysis and sorting using droplet-based microfluidics. Nat Protoc. May 2013;8(5):870-91.
Mitra et al., Fluorescent in situ sequencing on polymerase colonies. Anal Biochem. Sep. 1, 2003;320(1):55-65.
Notomi et al., Loop-mediated isothermal amplification of DNA. Nucleic Acids Res. Jun. 15, 2000;28(12):E63. 7 pages.
Parameswaran et al., A pyrosequencing-tailored nucleotide barcode design unveils opportunities for large-scale sample multiplexing. Nucleic Acids Res. 2007;35(19):e130. 9 pages.
Pooja et al., Loop-mediated isothermal amplification (LAMP) based detection of bacteria: A Review. African J Biotechnol. 2014. 13(19), 1920-1928.
Qiao et al., Rapid detection of Akabane virus by a novel reverse transcription loop-mediated isothermal amplification assay (RT-LAMP). Virol J. Sep. 14, 2013;10:288.

(56) References Cited

OTHER PUBLICATIONS

Qiu et al., DNA sequence-based "bar codes" for tracking the origins of expressed sequence tags from a maize cDNA library constructed using multiple mRNA sources. Plant Physiol. Oct. 2003;133(2):475-81.

Rotem et al., Single-cell ChIP-seq reveals cell subpopulations defined by chromatin state. Nat Biotechnol. Nov. 2015;33(11):1165-72.

Santesson et al., Cell-cell communication between adipocytes and pancreatic beta-cells in acoustically levitated droplets. Integr Biol (Camb). Oct. 2009;1(10):595-601.

Sarkar et al., T Cell Dynamic Activation and Functional Analysis in Nanoliter Droplet Microarray. J Clin Cell Immunol. Jun. 2015;6(3):334.

Shembekar et al., Droplet-based microfluidics in drug discovery, transcriptomics and high-throughput molecular genetics. Lab Chip. Apr. 21, 2016;16(8):1314-31.

Shendure et al., Accurate multiplex polony sequencing of an evolved bacterial genome. Science. Sep. 9, 2005;309(5741):1728-32.

Sjostrom et al., High-throughput screening for industrial enzyme production hosts by droplet microfluidics. Lab Chip. Feb. 21, 2014;14(4):806-13.

Sutcliffe et al., TOGA: an automated parsing technology for analyzing expression of nearly all genes. Proc Natl Acad Sci U S A. Feb. 29, 2000;97(5):1976-81.

Voelkerding et al., Next-generation sequencing: from basic research to diagnostics. Clin Chem. Apr. 2009;55(4):641-58.

Ziegenhain et al., Comparative Analysis of Single-Cell RNA Sequencing Methods. Mol Cell. Feb. 16, 2017;65(4):631-643.e4.

a.

b.

c.

A.

B.

A.

B.

C.

D.

A.

B.

C.

MULTI-DROPLET CAPTURE

The present application claims priority to U.S. Provisional application Ser. No. 62/612,755 filed Jan. 2, 2018, which is herein incorporated by reference in its entirety.

STATEMENT REGARDING FEDERAL FUNDING

This invention was made with government support under grant number CBET-1263889 awarded by the National Science Foundation. The government has certain rights in the invention.

FIELD

Provided herein are systems, methods, and articles of manufacture for collecting and merging two different size droplets using a substrate comprising a plurality of trapping sites. In certain embodiments, provided herein are systems composed of a plurality of larger droplets and smaller droplets and a substrate comprising a plurality of trapping sites where each trapping site is configured to trap only one of the larger droplets and only one of the smaller droplets when the larger droplet is already present at the trapping site. In particular embodiments, the larger and/or smaller droplets are sorted prior to being contacted with the substrate to ensure they contain the desired component (e.g., cell or barcoded bead). In other embodiments, each trapping site is composed of one or multiple fluidically linked capture wells. In some embodiments, collected larger and smaller droplets are merged (e.g., via a demulsifier or electricity).

BACKGROUND

Droplet-based microfluidics has been widely used in various biological assays at single-cell resolution such as antibody screening (1,2), enzyme screening (3), drug screening (4), genomics (5), transcriptomics (6), cell-cell interaction analysis (7-8). Droplet-based assays compartmentalize single cells in an immiscible two-phase flow and enables high-throughput analysis while preserving the characteristics of each cell in a small-volume droplet. The process of encapsulating cells in droplets is a stochastic process in which the number of cells (k) in a droplet follows a discrete probability distribution so called the Poisson distribution 9, given by:

$$P_\lambda(k, poission) = \frac{\lambda^k \exp(-\lambda)}{k!}, \quad (1)$$

where $\lambda$ is the average number of cells per droplet. Here, $\lambda$ is defined as $$\lambda = \frac{c}{V drop},$$

where c is the concentration of the cell suspension and V drop is the volume of each droplet. To avoid error caused by encapsulating more than a single cell in each droplet (k>1), one should flow cells at low concentration ($\lambda \ll 1$) such that $P(k>1, poission) \ll 1$. As a result, most of the droplets come out empty, which reduces the screening throughput and increases the reagent cost. This issue becomes more pronounced when the assay requires co-encapsulation of a pair of two particles in a common droplet.

Co-encapsulation of a cell-particle or cell-cell pair is a critical process in single-cell secretory analysis (1), single-cell mRNA sequencing (Drop-seq) (6), and cell-cell communication study (10). In most cases, the assay process strictly requires one-to-one pairing of either a cell and a particle or two cells to obtain unambiguous single cell study results. The conventional approach to pairing two distinct particles by a co-flowing scheme suffers from low pairing efficiency that results from multiplying the low-probability Poisson statistics of two rare events (FIG. 1a). As the outcomes are mostly negative droplets, including those with a single particle or doublet of particles of the same type, it causes sample lost and error in downstream analysis. The presence of such negative droplets also fundamentally eliminate the possibility to use active sorting to enrich the positive droplets with a pair of two desired particles (11,12).

To overcome the Poisson statistics limitation, a few studies have explored alternative encapsulation approaches. For example, Edd et al. (13) created self-ordered cell trains by a hydrodynamic effect and synchronized the process of injecting the cells into droplets at a flow-focusing zone with the droplet generation process at the same frequency. This approach resulted in high single-cell occupancy of the droplets. Later, Lagus et al. (14) demonstrated co-encapsulation of cell-cell pairs by co-flowing two distinct cell types based on a similar synchronization mechanism to the one above. Alternatively, Abate et al. (15), used mechanically deformable particles which can be closely packed in a channel to achieve ordered encapsulation to increase paring efficiency and accuracy. This method has been further applied to co-encapsulation of cell-bead pairs for inDrop single cell mRNA sequencing (16). However, all of these approaches need to satisfy stringent restrictions in practical applications. For example, forming the self-ordered cell trains requires size uniformity and high density of the cells. The closed-packed particles can only be made of soft materials, such as hydrogels. These approaches are all passive and therefore require such specific, well-controlled operation conditions to achieve an optimal result. Moreover, owing to the enormous time needed to adjust the balance between the aqueous and oil inflows, it is still challenging to obtain a high co-encapsulation yield with minimized sample loss with the existing approaches. What is needed is a more robust method that permits one-to-one encapsulation of desired objects.

SUMMARY

Provided herein are systems, methods, and articles of manufacture for collecting and merging two different size droplets using a substrate comprising a plurality of trapping sites. In certain embodiments, provided herein are systems composed of a plurality of larger droplets and smaller droplets and a substrate comprising a plurality of trapping sites where each trapping site is configured to trap only one of the larger droplets and only one of the smaller droplets when the larger droplet is already present at the trapping site. In particular embodiments, the larger and/or smaller droplets are sorted prior to being contacted with the substrate to ensure they contain the desired component (e.g., cell or barcoded bead). In other embodiments, each trapping site is composed of one or multiple fluidically linked capture wells. In some embodiments, collected larger and smaller droplets are merged (e.g., via a demulsifier or electricity).

In some embodiments, provided herein are systems comprising: a) a plurality of first droplets and a plurality of second droplets, wherein the second droplets are smaller than the first droplets (e.g., 10% ... 25% ... 50% ... 100% ... or 250% larger); b) a substrate comprising a plurality of trapping sites (e.g., at least 2 ... 15 ... 150 ... 2000 ... or 5000), wherein each of the trapping sites is configured to trap one and only one of the first droplets, and wherein each of the trapping sites is further configured to trap one and only one of the second droplets when a first droplet is present in the trapping site. In some embodiments, the ratio of the diameter of first (larger) droplets to the second (smaller) droplets is about 1.6-2:1 (e.g., 1.6 ... 1.8 ... 2.0 to 1).

In certain embodiments, the plurality of first droplets and/or the plurality of second droplets, each contain one, and only one, cell. In particular embodiments, the plurality of first droplets and/or the plurality of second droplets, each contain one, and only one, bead and/or type of nucleic acid barcode. In further embodiments, the plurality of first droplets each contain one, and only one, bead, and wherein the plurality of second droplets each contain one, and only one, cell. In certain embodiments, the plurality of first droplets and/or the plurality of second droplets each comprise water-in-oil droplets. In further embodiments, systems further comprise: c) a flow cell, wherein the substrate is located in the flow cell.

In certain embodiments, each of the plurality of trapping sites contains: i) one, and only one, first droplet, and ii) one, and only one, second droplet. In other embodiments, the systems further comprise: a plurality of third droplets, wherein the third droplets are smaller than the second droplets; and wherein each of the trapping sites is further configured to trap one and only one of the thirds droplets when both a first droplet and a second droplet is present in the trapping site.

In some embodiments, each of the plurality of trapping sites comprises one and only one capture-well. In additional embodiments, the plurality of trapping sites comprises a plurality of capture-wells. In other embodiments, each of the plurality of trapping sites comprises a first capture-well and a second capture-well, wherein the second capture-well is smaller in diameter than the first capture-well, and wherein first and second capture-wells are fluidically connected. In some embodiments, the first capture-well has a diameter between 10 μm and 300 μm (e.g., 10 ... 50 ... 150 ... 300 μm). In particular embodiments, the first capture-well has a diameter of 25-200 um. In certain embodiments, the first capture-well has a depth of between 5 and 250 μm (e.g., 5 ... 50 ... 125 ... 225 ... and 250 μm). In certain embodiments, the first capture-well has a depth of 25-200 um and a depth of 30-150 um. In some embodiments, the second capture-well has a diameter and/or depth of between 5 μm and 280 μm (e.g., 5 ... 25 ... 75 ... 150 ... 200 ... 225 ... and 280 μm). In some embodiments, the second capture-well has a diameter and/or depth of 25-120 um or 25-200 um. In particular embodiments, the first capture well is deeper than the second capture well. In other embodiments, the first capture well has the same depth as the second capture well. In additional embodiments, the plurality of first droplets have a diameter between 20 and 220 μm (e.g., 20 ... 25 ... 50 ... 75 ... 125 ... 155 ... 185 ... or 220), or said plurality of second droplets have a diameter between 20 and 220 μm (e.g., 20 ... 8 ... 50 ... 75 ... 125 ... and 220). In certain embodiments, the plurality of first droplets have a diameter of 45-200 um. In other embodiments, the plurality of second droplets have a diameter of 25-120 um.

In some embodiments, the first capture well has a liquid capacity between 30 picoliters and 10 nanoliters (e.g., 30 pL 250 pL 750 pL ... 1.0 nL ... and 10 nL), and/or wherein the second capture well has a liquid capacity of between 10 picoliters and 4 nanoliters (e.g., 30 pL 250 pL 750 pL ... 1.0 nL ... and 4 nL). In further embodiments, the plurality of trapping sites comprises at least 50 trapping sites (e.g., at least 50 ... 96 ... 382 ... 1000 ... 5000 ... 10,000 or more).

In particular embodiments, the systems further comprise: c) a container with at least one of the following: i) lysis reagents that allow mRNA and/or other bio-molecules to be released from cells; ii) a reverse transcriptase reagent; iii) RNA binding oligonucleotides comprising: a poly-T region and/or RNA-specific region; iv) a pool of oligonucleotides, each of which comprising a unique molecular identifier (UMI); v) primers or other oligonucleotides comprising a barcode sequence; and vi) reverse primers.

In certain embodiments, the systems further comprise: c) droplet-generating and/or sorting device. In other embodiments, the systems further comprise: a container comprising a demulsifier. In further embodiments, the substrate further comprises one or more flow channels. In additional embodiments, the substrate further comprises at least one embedded wire configured to deliver an electrical pulse to at least some of the plurality of trapping sites. In particular embodiments, each of the trapping sites are configured to trap one of the first droplets and one of the second droplets based on buoyancy of the first and second droplets in a carrier fluid. In further embodiments, the carrier fluid comprises oil.

In some embodiments, provided herein are methods: a) dispensing a plurality of first droplets into a flow cell containing a substrate which comprises a plurality of trapping sites such that one and only one of the first droplets is captured in each of the trapping sites; and b) dispensing a plurality of second droplets into the flow cell such that one and only one of the second droplets is captured in each of the trapping sites that contains one of the first droplets, wherein the second droplets are smaller than the first droplets.

In certain embodiments, any excess first droplets are flushed away from the substrate with a fluid after step a) but before step b). In some embodiments, any excess second droplets are flushed away from the substrate with a fluid after step b). In certain embodiments, the methods further comprise: c) treating the substrate such that the first and second droplets at each of the trapping sites merge into a single merged droplet, thereby generating a plurality of merged droplets. In certain embodiments, the treating comprises dispensing a demulsifier into the flow cell. In particular embodiments, the treating comprises providing the substrate with electricity. In further embodiments, the substrate comprises an embedded wire, and wherein the providing the substrate with electricity comprises sending an electric current through the embedded wire.

In some embodiments, the methods further comprise: d) dispensing a liquid comprising a surfactant into the flow cell such that the surfactant stabilizes the merged droplets. In additional embodiments, the method further comprise: d) collecting the merged droplets from the flow cell into a container. In other embodiments, the collecting comprises inverting the substrate such that the plurality of merged droplets float out of the plurality of trapping sites and are flowed out of the flow cell into the container. In additional embodiments, the plurality of first droplets and/or the plurality of second droplets, each contain one, and only one, cell. In certain embodiments, the plurality of first droplets and/or the plurality of second droplets, each contain one, and only one, bead and/or type of nucleic acid barcode. In further embodiments, the plurality of first droplets each contain one, and only one, bead, and wherein the plurality of second droplets each contain one, and only one, cell.

In some embodiments, the plurality of first droplets and/or the plurality of second droplets each comprise water-in-oil droplets. In certain embodiments, the methods further comprise: d) dispensing amplification reagents into the trapping sites. In other embodiments, the methods further comprise: e) treating the merged droplets at the trapping sites under conditions such that a sequencing library of sequencing templates is generated via an amplification reaction. In certain embodiments, each of the sequencing templates comprises: i) first and second barcode sequences, or complements thereof, and ii) a nucleic acid sequence of a coding region from an mRNA sequence, or complement thereof. In further embodiments, the methods further comprise: f) sequencing at least a portion of the sequencing library.

In some embodiments, provided herein are articles of manufacture comprising: a substrate, wherein the substrate comprises a plurality of trapping sites, wherein each of the trapping sites is configured to trap one and only one of a first-sized droplet (e.g., when the droplet is flowed over the substrate, such as in a flow cell), wherein each of the trapping sites is further configured to trap one and only one of a second-sized droplet when a first-sized droplet is present in the trapping site (e.g., when the droplet is flowed over the substrate, such as in a flow cell), and wherein the second-sized droplet is smaller than the first-sized droplet.

In certain embodiments, the substrate comprises silicone or plastic. In further embodiments, the substrate comprises a micro-well chip (e.g., such as the WAFERGEN SMART-CHIP which contains 5184 wells). In certain embodiments, the plurality of trapping sites comprises at least 25 trapping sites (e.g., at least 25 . . . 75 . . . 386 . . . 600 . . . 1000 . . . 4000 . . . 10,000 or more). In other embodiments, each of the plurality of trapping sites comprises a first capture-well and a second capture-well, wherein the second capture-well is smaller in diameter than the first capture-well, and wherein first and second capture-wells are fluidically connected. In some embodiments, the first capture-well has a diameter between 10 μm and 300 μm (e.g., 10 . . . 50 . . . 150 . . . 300 μm). In certain embodiments, the first capture-well has a depth of between 5 and 250 μm (e.g., 5 . . . 50 . . . 125 . . . 225 . . . and 250 μm). In some embodiments, the second capture-well has a diameter and/or depth of between 5 μm and 280 μm (e.g., 5 . . . 25 . . . 75 . . . 150 . . . 200 . . . 225 . . . and 280 μm). In certain embodiments, the first capture well is deeper than the second capture well. In further embodiments, the first capture well has the same depth as the second capture well. In some embodiments, the first capture well has a liquid capacity between 30 picoliters and 10 nanoliters (e.g., 30 pL . . . 250 pL . . . 750 pL . . . 1.0 nL . . . and 10 nL), and/or wherein the second capture well has a liquid capacity of between 10 picoliters and 4 nanoliters (e.g., 30 pL . . . 250 pL . . . 750 pL . . . 1.0 nL . . . and 4 nL). In some embodiments, the first sized droplet has a diameter between 20 and 220 μm (e.g., 20 . . . 50 . . . 100 . . . 150 . . . 220 μm). In additional embodiments, the second sized droplet has a diameter between 20 and 220 μm (e.g., 20 . . . 8 . . . 29 . . . 55 . . . 100 . . . 150 . . . 220 μm). In certain embodiments, the plurality of first droplets have a diameter of 45-200 um. In other embodiments, the plurality of second droplets have a diameter of 25-120 um.

In certain embodiments, the trapping sites comprise a reaction sample. In some embodiments, the reaction sample comprises at least one component selected from the group consisting of: a cell lysate, a cell, buffer, water, polymerase molecules, nucleic acid molecules, barcoded oligonucleotides, and detectable label molecules.

In certain embodiments, the substrate comprises heat conducting elements. In further embodiments, the substrate is set in a temperature controlling environment (e.g. a thermocycler or enclosed by heating-cooling plates). In some embodiments, substrate is set to different temperatures within the same and/or at different stages of one or multiple droplet fusion events.

BRIEF DESCRIPTION OF THE DRAWINGS

FIG. 1, panel a shows a conventional co-flow scheme for encapsulation of two distinct particles. Due to two independent Poisson events, the population of droplets containing a pair of two distinct particles constitutes a small fraction. FIG. 1, panel b shows an approach that first involves sorting of single-particle encapsulating droplets, which is followed by paring and merging of two sorted droplets, each containing a different particle. As a result, nearly 100% of the sorted droplets contains only one particle. Then, the merged droplets turn out to contain exactly two distinct particles. FIG. 1, panel c shows a CAD layout of droplet generating/sorting device (top view). FIG. 1, panel d shows dimensions of flow-focusing zone. For generating larger (80 μm) droplets: B=C=60 μm, A=D=70 μm, channel height=70 μm. For smaller (40 μm) droplets: A=B=30 μm, C=25 μm, D=40 μm, channel height=45 μm.

FIGS. 3b and 3c show images of droplets generated from the droplet generating/sorting devices described in Example 1. FIG. 3b shows 80 μm-diameter droplets containing microbeads. About 98% of droplets contain one or more than one beads. FIG. 3c shows 40 μm-diameter droplets containing cells. About 99.94% of droplets contain one or more than one cells.

DEFINITIONS

Figure 1:
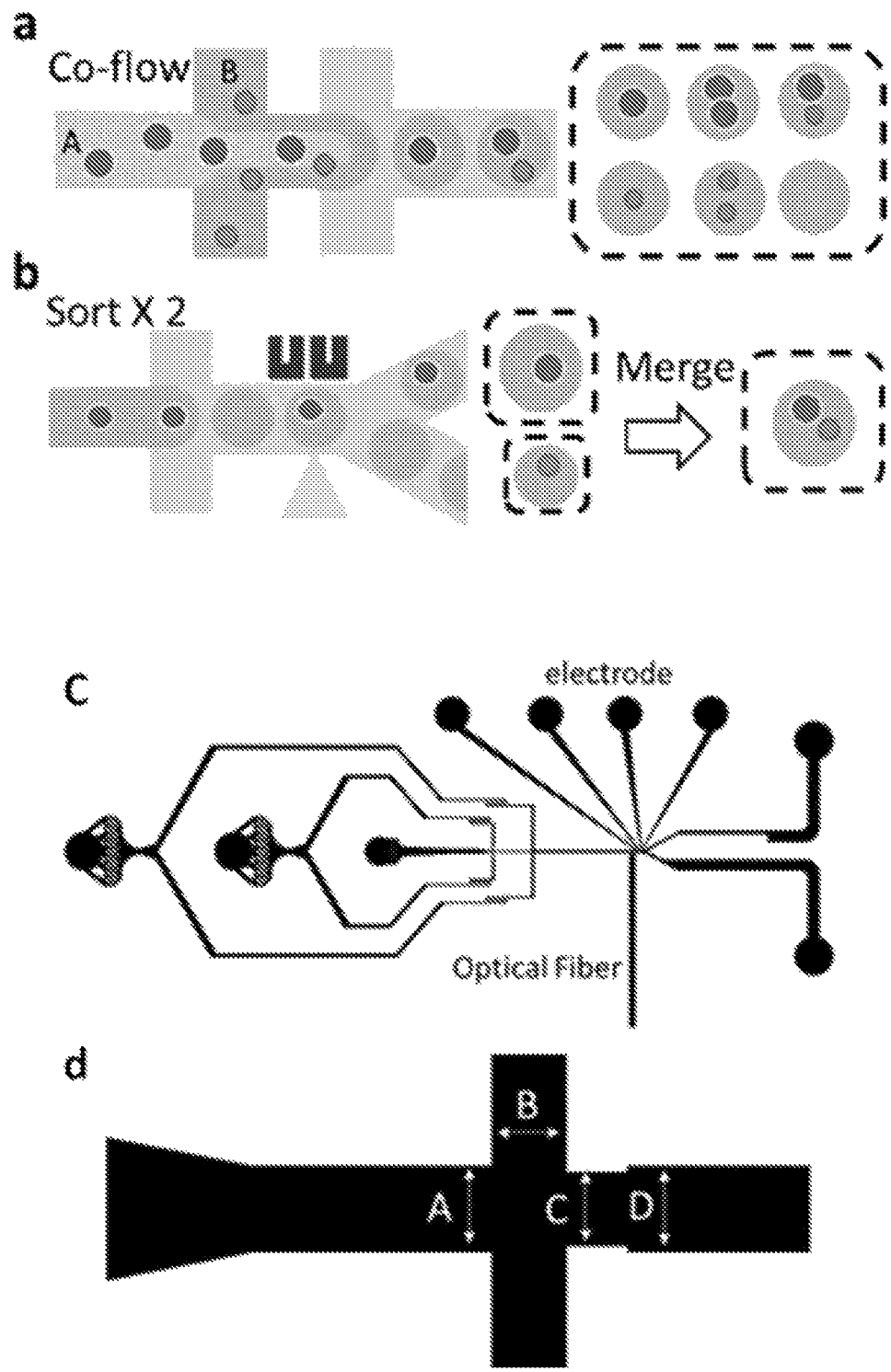
FIG. 1, panels a-d.

As used herein, the term "barcode" refers to a nucleic acid sequence that allows some feature of a polynucleotide with which the barcode is associated to be identified. In some embodiments, the feature of the polynucleotide to be identified is the sample (e.g., cell) or well (e.g., on a multi-well device) from which the polynucleotide is derived. In some embodiments, barcodes are about or at least about 3, 4, 5, 6, 7, 8, 9, 10, 11, 12, 13, 14, 15, or more nucleotides in length. In some embodiments, barcodes are shorter than 10, 9, 8, 7, 6, or 5 nucleotides in length. In some embodiments, barcodes associated with some polynucleotides are of different lengths than barcodes associated with other polynucleotides. In general, barcodes are of sufficient length and comprise sequences that are sufficiently different to allow the identification of samples based on barcodes with which they are associated. In some embodiments, each barcode in a plurality of barcodes differs from every other barcode in the plurality (e.g., at least one nucleotide position, such as at least 2, 3, 4, 5, 6, 7, 8, 9, 10, or more nucleotide positions. A plurality of barcodes may be represented in a pool of samples, each sample comprising polynucleotides comprising one or more barcodes that differ from the barcodes contained in the polynucleotides derived from the other samples in the pool. Samples of polynucleotides comprising one or more barcodes can be pooled, and subsequently identified based on the barcode sequences to which they are joined. In general, a barcode comprises a nucleic acid sequence that when joined to a target polynucleotide serves as an identifier of the sample or well from which the target polynucleotide was derived.

As used herein the term "primer" refers to an oligonucleotide that can be used in an amplification method, such as a polymerase chain reaction (PCR), to amplify a nucleotide sequence. Typically, at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art.

As used herein, the term "primer pair" or "pair of primers" refers to two primers, a forward primer and a reverse primer, which, when exposed to an appropriate target nucleic acid under the proper conditions, may be used to amplify a portion of the target nucleic acid.

As used herein, the term "primer set" or "set of primers" refers to two or more primers, which, while not identical in sequence over their full length (e.g., comprising different barcode sequences or UMIs), bind to the same hybridization site on a target nucleic acid and perform the same role (e.g., forward primer, reverse primer, etc.) in an amplification reaction.

DETAILED DESCRIPTION

Provided herein are systems, methods, and articles of manufacture for collecting and merging two different size droplets using a substrate comprising a plurality of trapping sites. In certain embodiments, provided herein are systems composed of a plurality of larger droplets and smaller droplets and a substrate comprising a plurality of trapping sites where each trapping site is configured to trap only one of the larger droplets and only one of the smaller droplets when the larger droplet is already present at the trapping site. In particular embodiments, the larger and/or smaller droplets are sorted prior to being contacted with the substrate to ensure they contain the desired component (e.g., cell or barcoded bead). In other embodiments, each trapping site is composed of one or multiple fluidically linked capture wells. In some embodiments, collected larger and smaller droplets are merged (e.g., via a demulsifier or electricity).

Co-encapsulation of two (or more) distinct particles in microfluidic droplets provides a way to achieve various high-throughput single-cell assays, such as biochemical reaction and cell-cell interaction in tiny isolated volumes. However, limited by the Poisson statistics, the co-encapsulation rate of the conventional co-flow approach is low even under the optimal conditions. Only up to 13.5% of droplets contains exactly one of each particle, while the rest, either being empty or containing unpaired particles becomes wastes. Thus, the low co-encapsulation efficiency makes droplet-based assays impractical in biological applications involving low abundant cells. Provided herein are methods, systems, articles, and composition that provide a droplet merging strategy to increase the co-encapsulation efficiency (see, e.g., FIG. 1b).

In certain embodiments, provided herein are methods that generates two different types of droplets (or three or four or more), for example, containing either a single cell or a single bead individually and eliminates empty droplets by photo-activated droplet sorting (or other types of sorting). Next, the two (or more) different types of droplets are paired on a one-to-one basis and merged to generate droplets that contain exactly two (or more) different objects. Traditionally, efficient post-sorting droplet merging has been perceived as an unfeasible approach because it requires highly challenging off-chip handling of a tiny total volume of sorted droplets (for example, 1,000 of 50 um droplets are only 65 nl in total volume) and precise one-to-one pairing. While a serial paring method, which requires synchronization of two droplet trains (17) appears to work well for a large number of droplets, its overall recovery rate is low due to droplet lost in flow adjusting steps, therefore, is not feasible for merging small amount of droplets. Although a parallel merging approach may handle a small amount of droplets better (18,19) its co-encapsulation efficiency was not reported. The methods and systems herein allow, for example, seamless droplet generation, sorting, capturing, pairing, and merging in one system to reduce the complexity of the assay. The desired particles are actively selected and one-to-one paired precisely inside the droplets, therefore, overcomes sample loss due to Poisson statistics.

In certain embodiments, the droplets are sorted prior to being exposed to the substrate. In certain embodiments, droplets that contain a desired component (e.g., single cell, barcode, bead, or other reagent) are sorted to collect only the desired droplets, which are then flowed over the substrates contained herein. In certain embodiments, the sorting methods are as described in WO2016193758, which is herein incorporated by reference in its entirety, particularly with respect to the droplet sorting methods described therein.

Figure 8:
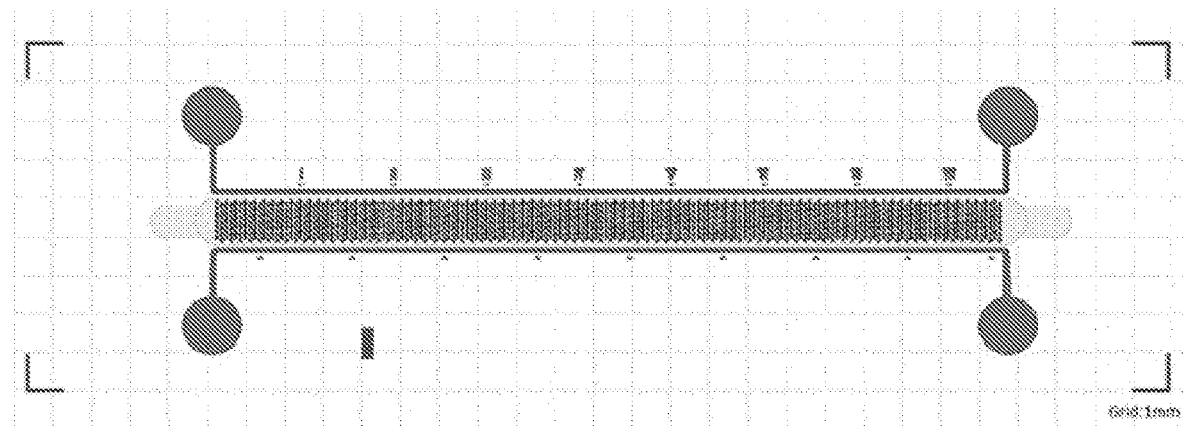
FIG. 8A shows a multi-well array that includes a pair of embedded electrical wires along each side which enables multiple rounds of precise droplet merging via electrical pulses (causes droplet fusion by dielectric force).
FIG. 8B left side shows a close up view of the multi-well array in FIG. 8A, and the right side of FIG. 8B shows a transmit light image of a the multi-well array. Arrows indicate electrical wires that connect to high voltage power.
Figure 8:
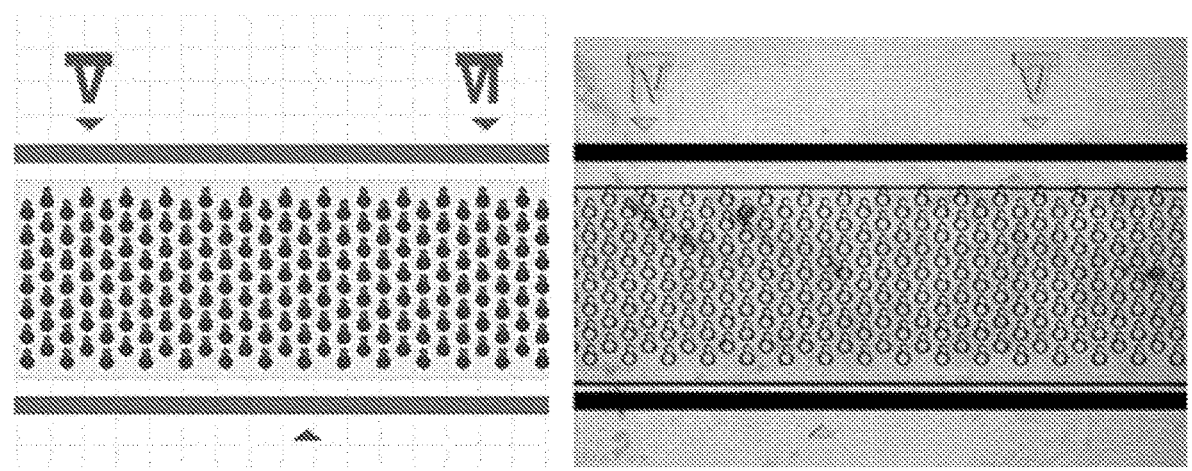
Figure 9:
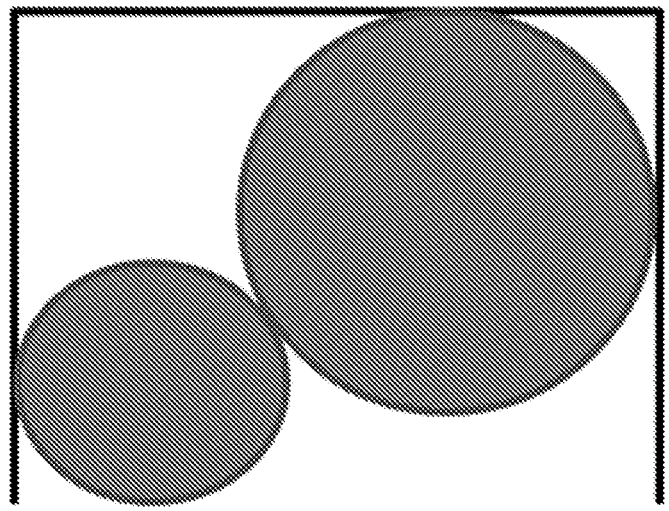
FIG. 9A shows a side view of an exemplary trapping site which is a micro-well sized to receive only one larger droplet (floating up by buoyancy of the droplet), and receive only one smaller sized droplet once the larger droplet is in place (again, floating up by buoyancy of the droplet).
FIG. 9B shows the same exemplary trapping site, except the larger and smaller droplets are trapped by gravity rather than buoyancy.
FIG. 9C shows a top view of an exemplary trapping site composed of three interlinked micro-wells, sized to first capture only one largest droplet (e.g., 80 um in diameter) flowed in first, then capture only one medium sized droplet (e.g., 40 um in diameter) flowed in second, and finally to capture only one smallest droplet (e.g., 20 um in diameter) flowed in third. The three captured droplets can be merged as described herein (e.g., by providing a demulsifier or an electric charge).
FIG. 9D shows an exemplary trapping site that adds a fourth micro-well to the trapping site shown in FIG. 9C. This fourth micro-well receives a droplet even smaller than the smallest droplet in FIG. 9C (e.g., with a diameter of 8 um) and is flowed in last. Additional embodiments adding further smaller wells (e.g., that serve to trap 5, 6, 7 or more droplets) can be constructed and employed in the methods herein.
Figure 9:
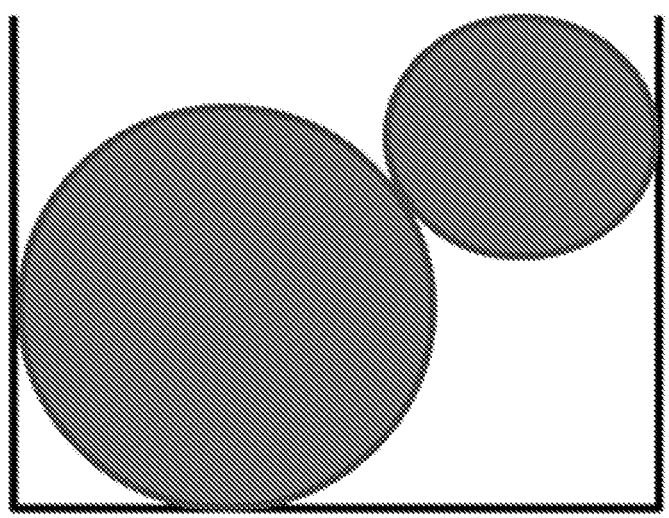
Figure 9:
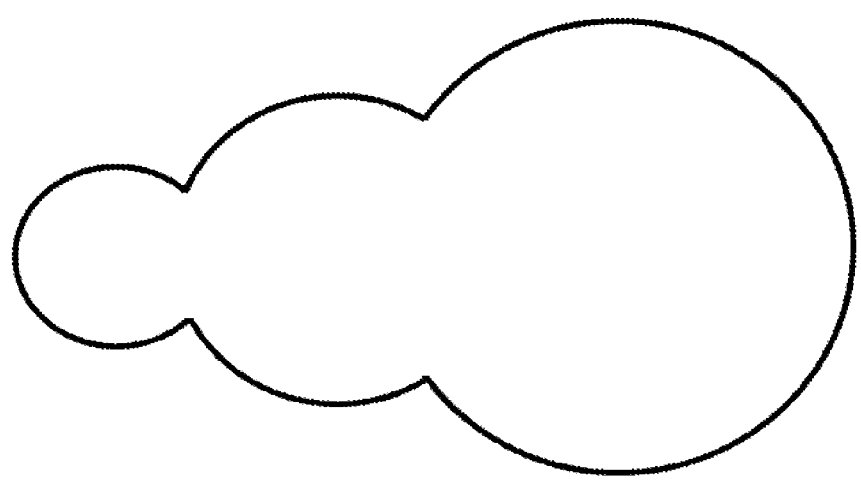
Figure 9:
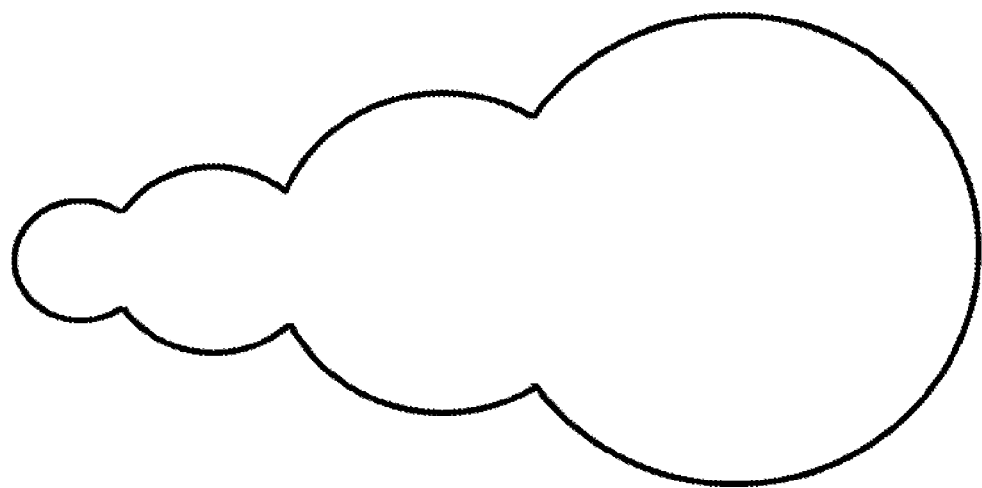

In certain embodiments, once two (or more) droplets are present together at a trapping site, they can be merged, such as by using a demulsifier or an electric current. One exemplary protocol using the electric current device shown in FIG. 8 is follows. In this exemplary protocol, the merging device in FIG. 8 allows a protocol to perform sequential operations of in-droplet PCR followed by in-droplet reverse-transcription to increase probing efficiency and gene coverage for the droplet-based high-throughput single cell mRNA sequencing. This protocol allows one to first generate larger (e.g., 80 micron) droplets in which a cell barcoded synthesized bead (similar, but complementary to those used in the "Drop-seq" paper, Cell 2015, 161:1202-1214, herein incorporated by reference) and PCR reagents are included. The PCR step amplifies the cell barcodes from the synthesis bead into tens of folds concentrated free cell barcode primers in droplet solution. After sorting these larger (e.g., 80 um) droplets into the merging device to complete fill up the larger wells, one sorts smaller (e.g., 40 um) droplets, which contains reagent for cell lysis and reverse transcription and use a chain of electrical pulses delivered through the imbedded wire to allow droplet fusion by dielectric force (see device in FIG. 8). This step is important because it allows separating the loading of temperature sensitive reverse transcription reagent from the PCR reaction. Since fused droplets are no longer destabilized, they are suitable for next round of fusion, until the merged droplet is too big to fit into the well. Therefore, one can sort even smaller (e.g., 40 um) droplets, each of which contains single fluorescent single cell into the same device to allow fusion to the primer-amplifier (by PCR) droplets for highly efficient priming and gene recovery. The PCR step is important because it overcomes two major limitations of using primer-bead: 1) it provides many fold higher concentration of reverse transcription primer for the reverse transcription, and 2) it transforms the reverse transcription into solution, which eliminated the space limitation on the bead for priming mRNAs and increases priming efficiency because short primers are more freely diffusing to hybridize onto the much larger mRNA molecules.

In certain embodiments, the substrates herein comprise a plurality of trapping sites. In certain embodiments, the substrates are multi-well devices (e.g., plates or chips). The overall size of the substrates herein (that contain a plurality of trapping sites) may vary and it can range, for example, from a few microns to a few millimeters or centimeters in thickness, and from a few microns to 50 millimeters or centimeters in width or length. Typically, the size of the entire device containing the substrate ranges from about 10 mm to about 200 mm in width and/or length, and about 1 mm to about 10 mm in thickness. In some embodiments, the substrate (e.g., chip) is about 40 mm in width by 40 mm in length by 3 mm in thickness.

The total number of capture-wells on the substrate may vary depending on the particular application in which the device is to be employed. The density of the capture-wells in the array may vary depending on the particular application. The density of capture-wells, and the size and volume of capture-wells, may vary depending on the desired application and such factors as, for example, the species of the organism for which the methods of this invention are to be employed (e.g., for embodiments in which a cell is deposited into the capture-well), the type of reaction to be performed in the well, the detection technique, etc.

Figure 10:
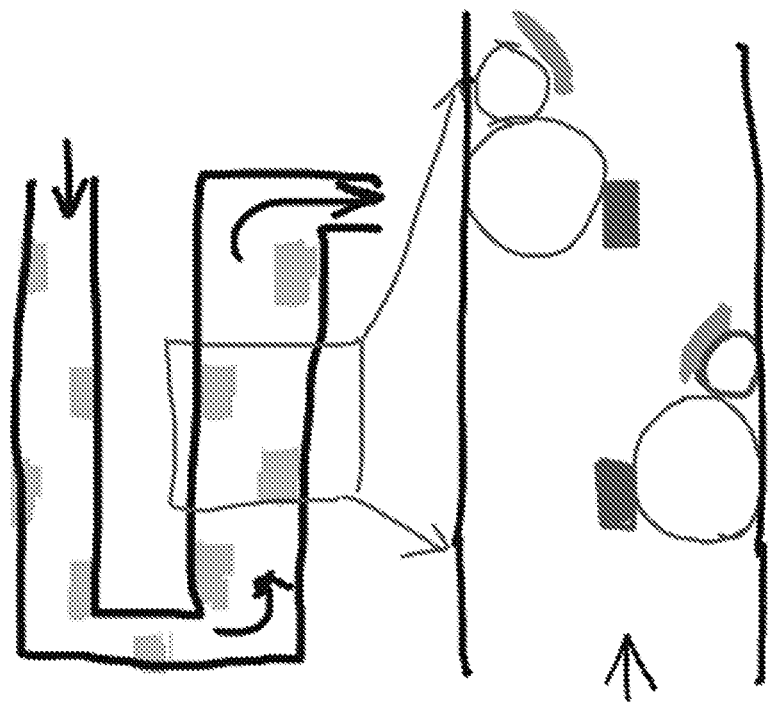
FIG. 10A, left side, shows a top view of an exemplary flow cell containing various trapping sites. The trapping sites are shown on the right side of FIG. 10A as being composed of two merged micro-wells (a smaller well linked to a larger well) as well as trapping pegs (square and oblong) situated to collect droplets into the trapping cells. In operation, the smaller sized droplets (e.g., containing a cell) are loaded into the flow cell first.
FIG. 10B shows how once a smaller droplet occupies the smaller micro-well, the other smaller droplets are blocked from occupying the same well and flow out between the oblong and square trapping pegs until being trapped by a subsequent unoccupied smaller well (shown by dotted smaller droplets).
FIG. 10C shows the second step where the larger droplets (e.g., containing a barcode) are flowed into the flow cell and how they occupy the large microwells. Once a larger droplet is trapped, the other larger droplets will flow by that occupied well and will be trapped by a subsequent empty larger well (shown by dotted larger droplets). The captured droplets may be merged (e.g., by a demulsifier or electricity) as described herein.
Figure 10:
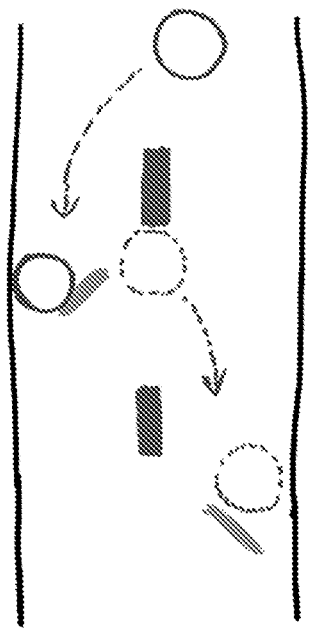
Figure 10:
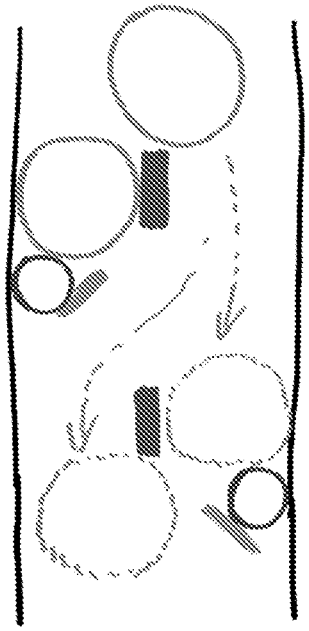

The present invention is not limited by the number of capture-wells in the substrate. A large number of wells may be incorporated into a device. In various embodiments, the total number of capture-wells on the device is from about 100 to about 2,000 or from about 5,000 to about 100,000 (e.g., 9600 wells, 35400 well, or 153,600 wells). For example, a square chip may comprise 125 by 125 capture-wells. In some embodiments, the arrays of capture-wells are arranged into columns and rows. A substrate may comprise any suitable number of array columns, for example: 2, 4, 8, 12, 16, 24, 36, 48, 64, 72, 96, 100, 120, 196, >250, or any number or columns (e.g., 50) or ranges (e.g., 16-96, 48-196, etc.) therein. A substrate may comprise any suitable number of rows, for example: 2, 4, 8, 12, 16, 24, 36, 48, 64, 72, 96, 100, 120, 196, >250, or any number or rows (e.g., 50) or ranges (e.g., 16-96, 48-196, etc.) therein. In some embodiments, the columns and/or rows of arrays are arranged to form an X/Y grid with rows running perpendicular to columns. In other embodiments, rows and/or columns are offset. In such embodiments, columns and rows may be at a non-perpendicular orientation with respect to each other (e.g., <90°). In other such embodiments, columns and/or rows may form a zig-zag rather than a straight line. In other embodiments, capture-wells may be fabricated in a single channel and arranged as a zig-zag tunnel, as demonstrated in FIG. 10*a*.

The capture-wells in the substrate may be fabricated in any convenient size, shape or volume. The transverse sectional area may be circular, elliptical, oval, conical, rectangular, triangular, polyhedral, or in any other shape. The transverse area at any given depth of the well may also vary in size and shape. The cavity of each capture-well may take a variety of configurations. For instance, the cavity within a capture-well may be divided by linear or curved walls to form separate but adjacent compartments, or by circular walls to form inner and outer annular compartments. In certain embodiments, a portion of a side-well of a capture-well is reduced in side such that it is fluidically linked to an adjacent (e.g., smaller) capture-well.

A well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, AQUASIL, and SURFASIL. Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions.

An exemplary substrate (with a plurality of trapping sites) may have a thickness of about 0.5 mm to 10 mm (e.g. 3.5 mm). The length and width of the substrate may be the same or about the same size as an SBS-compliant plate (e.g., 96 well plate, 384 well plate, or a 1536 well plate). The capture-wells of the substrate may be formed using, for example, commonly known photolithography techniques. The capture-wells may be formed, for example, using a wet KOH etching technique, an anisotropic dry etching technique, mechanical drilling, injection molding and or thermo forming (e.g., hot embossing).

In some embodiments, a sample is contained in a droplet, or deposited via droplets, into all or a portion of the capture-well of a substrate (or the sample is already present in a capture-well). For example, a sample comprising nucleic acid (e.g., DNA, RNA, etc.) is contained or deposited in the capture-wells. Similar or identical samples may be within all or a portion of the capture-wells or distinct samples may be within the different capture-wells. In some embodiments, a sample comprises cells. In some embodiments, a single cell is deposited into each capture-well. In some embodiments, capture-wells comprise a cell lysate. Lysis of a cell or cells may occur within the capture-well or a cell lysate may be deposited into the capture-wells. In particular embodiments, a single cell is deposited into each capture-well via a droplet, and the cells are subsequently lysed in the capture-wells to produce a single-cell lysate in each well.

In some embodiments, a primer comprises a segment that serves as a unique molecular identifier (UMI), which is provided to a capture-well via a droplet, or already present in a capture-well. A UMI is a randomized nucleic acid sequence that is unique for every primer in a primer set. The UMI allows for identification and/or differentiation of specific amplified products, even when they are generated in the same reaction or reaction conditions. A UMI is typically 4-20 nucleotides in length (e.g., 4, 5, 6, 7, 8, 9, 10, 11, 12, 13, 14, 15, 16, 17, 18, 19, 20, or ranges therebetween). The length of the UMI may be selected based on the number of capture-wells or nucleic acid products to be produced, such that each primer, and therefore each nucleic acid product, will statistically have a unique and distinguishable UMI.

In some embodiments, a primer comprises one or more barcoding sequences, which is provided to a capture-well via droplet or already present in a capture-well. In some embodiments, the barcode sequence is a nucleic acid segment that allows identification of the source of an amplified product nucleic acid (e.g., after it is pooled using the systems and methods described herein). For example, in some embodiments, a barcode allows a sequenced cDNA to be correlated to the cell, well, sub-array, a substrate herein, and/or experiment from which it was generated. In some embodiments, a barcode is correlated to one or more features of a nucleic acid, such as, the cell-type from which it was derived, the conditions the nucleic acid or cell were exposed to, the date it was generated, or the substrate in which it generated, or the capture-well in which it generated. In some embodiments, a primer (or primer pair) comprises multiple barcode sequences that correlate to multiple pieces of information about the nucleic acid target. In particular embodiments, the first primer of a primer pair comprises at least one barcode and the second primer of the primer pair comprises at least a second barcode (e.g., correlating to the individual capture-wells from which it was from). The feature-denoting sequence (e.g., barcode) may be of any suitable length in order to provide source-well identification based thereon. For example, in some embodiments, feature-denoting sequence (e.g., barcode) is 3-10 nucleotides in length (e.g., 3, 4, 5, 6, 7, 8, 9, 10, or any ranges therebetween (e.g., 4-8, 3-6, etc.)).

In some embodiments, reagents are contained and/or added to the capture-wells of a substrate for nucleic acid amplification/analysis. Reagents contained within the liquid in the substrate depend on the reaction that is to be run therein. In an embodiment, the capture-wells contain a reagent for conducting the nucleic acid amplification reaction. Reagents can be reagents for immunoassays, nucleic acid detection assays including but not limited to nucleic acid amplification. Reagents can be in a dry state or a liquid state in a unit of the device. In an embodiment, the capture-wells contain at least one of the following reagents: a probe, a polymerase, and dNTPs. In another embodiment, the wells contain a solution comprising a probe, a primer and a polymerase. In various embodiments, each capture-well comprises a primer for a polynucleotide target within a genome, and a probe associated with the primer which emits a concentration dependent signal if the primer binds with the target. In another embodiment, at least one capture-well of the substrate contains a solution that comprises a forward PCR primer, a reverse PCR primer, and at least one FAM labeled MGB quenched PCR probe. In an embodiment, primer pairs are dispensed into a capture-well and then dried, such as by freezing. The user can then selectively dispense, such as nano-dispense, the sample, probe and/or polymerase.

In other embodiments of the invention, the capture-wells may contain any of the above solutions in a dried form. In this embodiment, this dried form may be coated to the capture-wells or be directed to the bottom of the capture-well. The user adds a droplet containing a liquid sample (e.g., water, buffer, biological or environmental sample, mixture of water and the captured cells, etc.) to each of the capture-wells before analysis. In this embodiment, the substrate comprising the dried down reaction mixture may be sealed with a liner, stored or shipped to another location.

The substrates containing a nucleic acid sample (e.g., with a single cell in each capture-well), may be used for genotyping, gene expression, or other DNA assays performed by PCR. Assays performed in the plate are not limited to DNA assays such as TAQMAN, TAQMAN Gold, SYBR gold, and SYBR green but also include other assays such as receptor binding, enzyme, and other high throughput screening assays. In some embodiments, a ROX labeled probe is used as an internal standard.

In certain embodiments, reagents for nucleic acid analysis, sequencing, amplification, detection, etc. are added to the capture-wells comprising nucleic acid sample (e.g., lysate from a single cell per well). In some embodiments, such reagents include components that employ barcoding for labelling nucleic acids (e.g., mRNA molecules) and/or for labeling for cell/well source, and/or for labeling particular sub-arrays sources in multi-well devices, so as to distinguish various labeled oligonucleotides after they are pooled using the systems described herein. Examples of such barcoding methodologies and reagents are found in, for example, Pat. Pub. US2007/0020640, Pat. Pub. 2012/0010091, U.S. Pat. Nos. 8,835,358, 8,481,292, Qiu et al. (Plant. Physiol., 133, 475-481, 2003), Parameswaran et al. (Nucleic Acids Res.

2007 October; 35(19): e130), Craig et al. reference (Nat. Methods, 2008, October, 5(10):887-893), Bontoux et al. (Lab Chip, 2008, 8:443-450), Esumi et al. (Neuro. Res., 2008, 60:439-451), Hug et al., J. Theor., Biol., 2003, 221: 615-624), Sutcliffe et al. (PNAS, 97(5):1976-1981; 2000), Hollas and Schuler (Lecture Notes in Computer Science Volume 2812, 2003, pp 55-62), and WO2014201272; all of which are herein incorporated by reference in their entireties, including for reaction conditions and reagents related to barcoding and sequencing of nucleic acids.

In some embodiments, nucleic acid from capture-wells is sequenced. A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695, 934; 5,714,330; herein incorporated by reference in their entireties) and the Adessi PCR colony technology (Adessi et al. (2000). Nucleic Acid Res. 28, E87; WO 00018957; herein incorporated by reference in its entirety). A set of methods referred to as "next-generation sequencing" techniques have emerged that may also be employed (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, Pacific Biosciences (PAC BIO RS II) and other platforms commercialized.

In certain embodiments, the microfluidic devices described herein, composed of a substrate with a plurality of trapping sites, are made with multilayer soft lithography techniques. One example of such a technique is as follows. To make the mold with microfluidic pattern, SU-8 photoresist is spin-coated onto 4-inch silicon wafers. The thickness of photoresist film can be varied with repeated coating of SU-8 photoresist, spinning time, and spinning speed. After baking, the additional solvent in photoresist is evaporated and the photoresist is exposed under UV light to initiate cross-linking. Then, the post-exposure bake process is applied to cure the exposed area, forming permanent cross-linked epoxy. Finally, the residual photoresist is washed out by MicroChem's SU-8 developer and isopropanol. (see, e.g., detailed parameters for processing time, temperature . . . etc. in Microchem's manual). After the Su-8 molds are ready, the Polydimethylsiloxane (Dow Corning, Sylgard 184) and curing agent are mixed at 10:1 ratio, poured on the Su-8 mold, and baked at 65° C. for 8 hours to replicate the microfluidic channel. The cured PDMS is punched with 0.75 mm biopsy puncher to form inlets/outlets. Two layers of PDMS containing microwells array and fluidic channel are bonded to a glass slide with the surface activation by oxygen plasma subsequently (Femto Scientific Inc.), as shown, for example in FIG. 2F. Microelectrodes are created by injecting low melting alloy (e.g., 247 solder) into the microchannels (e.g., as shown in FIG. 8A) at 150° C. In other embodiments, the microfluidic devices could alternatively be made by other methods, such as precision injecting-molding of thermoplastic polycarbonate (PC) and epoxy bonding, precision 3D printing of PC, and laser micromachining of glass.

EXAMPLES

Example 1

Dual Droplet Capture and Merging on a Multi-Trapping Site Substrate

This Example describes systems and methods for dual droplet capture on a multi-trapping site substrate, and merging of such co-captured droplets.

Methods

Microfluidic System

Figure 2:
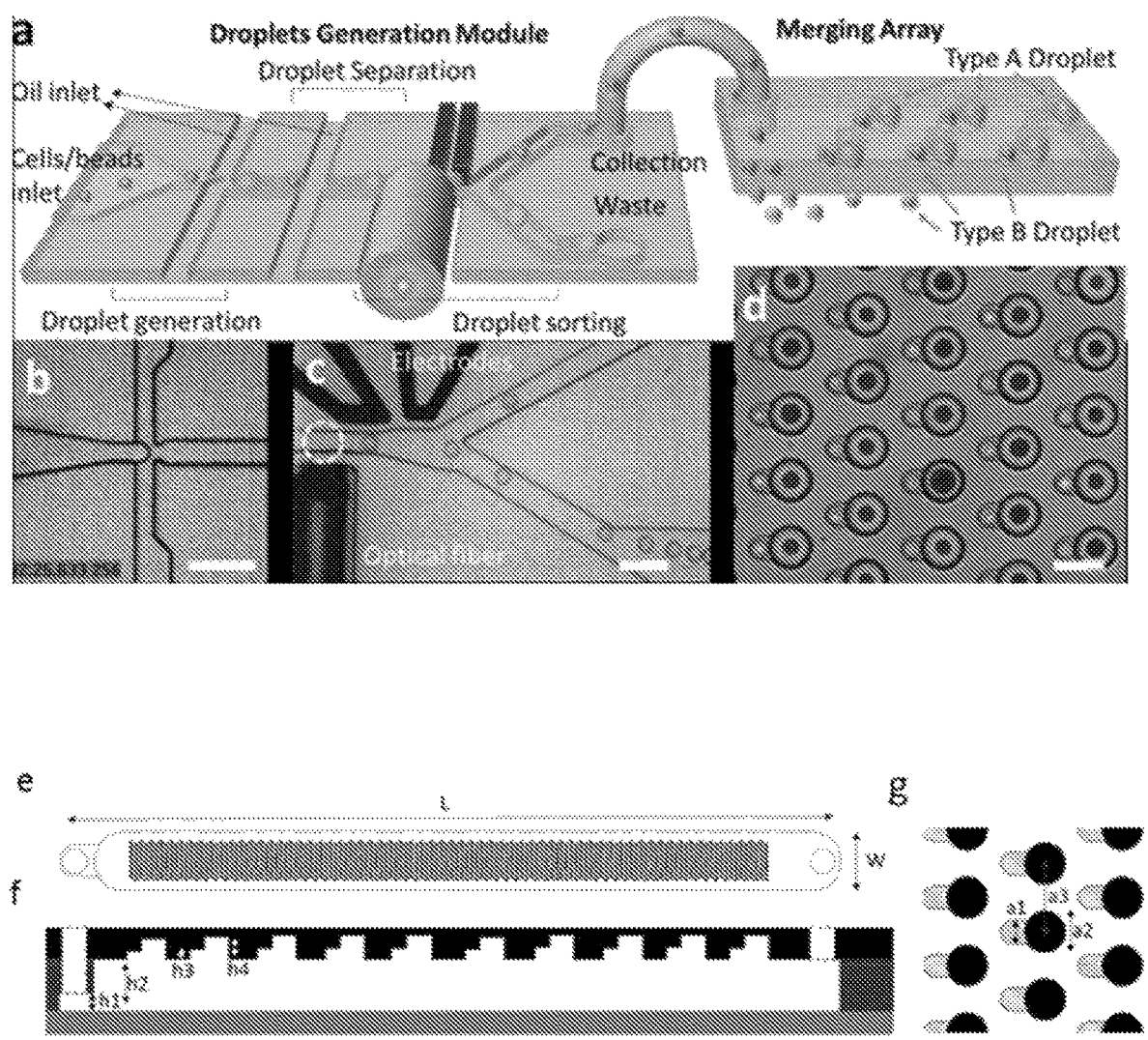
FIG. 2a shows an exemplary schematic of one embodiment of a microfluidic system composed of droplet generating/sorting and droplet merging devices.
FIG. 2b shows an exemplary droplet generation process. Water-in-oil droplets, each containing a single particle, are generated at the flow-focusing structure.
FIG. 2C shows an exemplary droplet sorting process. The droplets generated in (b) are sorted to the upper outlet channel connected to the downstream droplet merging device by photo-activated sorting. The white dashed circle indicates the position of the interrogation zone next to the embedded optical fiber illuminating laser light and collecting a droplet optical signal. The merging device is composited of 1152 trapping sites where droplets of two different sizes are captured and paired.
FIG. 2d shows an image of 40 um-diameter single-cell containing droplets paired with 80 um-diameter microbead containing droplets at the merging device. Scale bar:100 μm.
FIG. 2e shows a top view of an exemplary droplet merging device. The outside line represents the microfluidic channel structure and the internal patterns represent the array of microwells. L=25 mm, w=2 mm. Array size=9 rows×128 columns=1152 microwells.
FIG. 2f shows a side view of the device (the drawing is not to scale). h1=100 μm, h2=500 μm, h3=40 μm, h4=70 μm.
FIG. 2g shows the lattice structure of the array. a1=45 μm, a2=80 μm, a3=140 μm.

The exemplary microfluidic system employed in this example is composed of two sub-component devices: a droplet generating device with a built-in photo-activated sorting function (FIG. 2a-c) and its collection output-connected droplet merging device (FIG. 2a, d). Both of these devices are made of Polydimethylsiloxane (PDMS) by the standard soft lithography method, and the microelectrodes are fabricated using a solder iron. The channels of all the devices are silanized with Trichloro(1H,1H,2H,2H-perfluorooctyl) silane to prevent droplets wetting.

Droplet Generating/Sorting Device

The droplet generating/sorting device incorporates an active droplet sorting function (20) by which only desired droplets are selected and guided to its collection channel. We use two nozzles of different sizes (FIG. 1C) for the device's flow-focusing zone structure to generate water-in-oil (HFE 7500, 3M) droplets with two distinct sizes of 80 µm and 40 µm in diameter. The droplets are stabilized with 2% EA surfactant (RAN biotech.) in the oil. Once the droplets move to the interrogation zone in front of an embedded optical fiber (F-MCB-T, Newport), they are illuminated by a laser beam (450 nm, 50 mW) focused by 10× objectives (FIG. 1d). The fluorescent and scattering light are collected by an optical fiber and detected by two photomultiplier tubes (H9306-03, Hamamatsu). A dichroic mirror (500LP) and two bandpass filters (CW450 nm and 525 nm) are used to separate fluorescent and scattering light. The signal will then be processed in real time by an electrical circuit. The droplets emitting desired signal will trigger a high-voltage AC pulse (<2 kVpp, 30 kHz) at microelectrodes. The dielectrophoresis effect due to a strong AC electric field around the microelectrodes pulls the signal-emitting droplets into the collection channel while the empty droplets simply flow into the waste channel following lower fluidic resistance (FIG. 1c).

Droplet Merging Device

Figure 4:
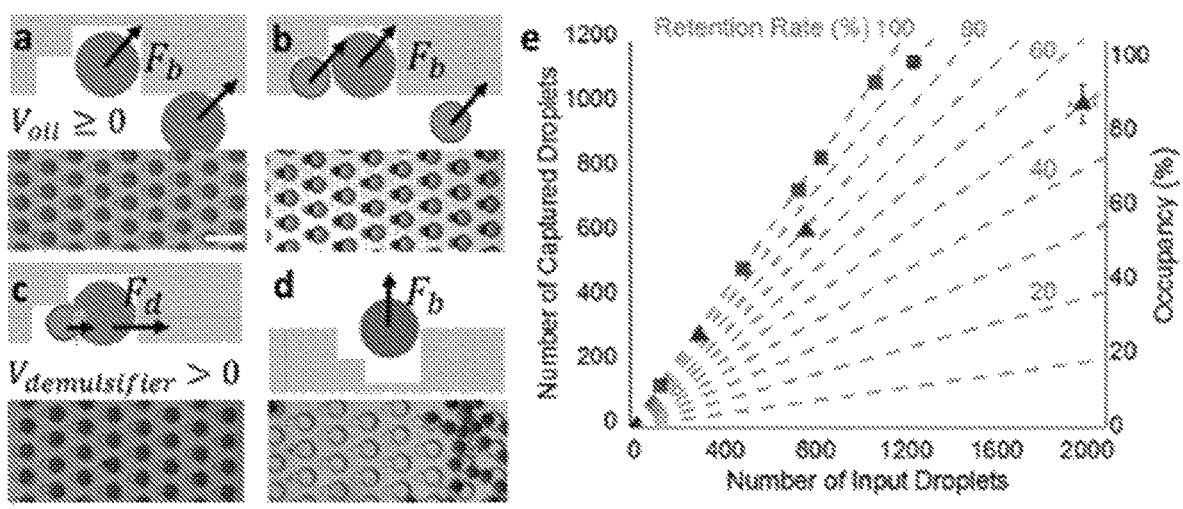
FIG. 4a-d shows sequential schematics (side-view) and images (top-view) of exemplary droplet capturing, pairing, and merging steps. The black arrow indicates the dominated force in each step. (a) 80 μm-(larger) droplets introduced to the droplet merging device first settle in the trapping sites by buoyance force. The flow speed in the bottom channel is nearly zero during droplet capturing and >0 while washing uncaptured droplets. (b) Similarly, 40 μm-(smaller) droplets are captured and paired with the larger droplets already captured in the trapping sites. (c) An external flow containing demulsifier is used to make two paired droplets in contact by drag force and merge them. (d) After re-stabilizing them, the droplets can be released by flipping the device. (e) The number of input droplets versus the number of captured droplets in a merging device of 1152 microwells. The larger and smaller dots indicate 80 μm (larger) and 40 μm (smaller) droplets, respectively. The retention rate (gray dash line) is defined as the number of captured droplets/the number of input droplets. The occupancy (right axis) is defined as the number of captured droplets/the number of available capturing sites.

The droplet merging device is a flowing channel that contains a uniquely designed 1152-microwell array located at the top of the channel. Directly connected to the upstream collection channel, the merging device captures droplets by buoyancy trap. The carrier fluid in this Example is 3M Novec HFE7500 oil (it is noted that other fluorocarbon oils could be employed, such as FC40). Each microwell is designed to fit exactly two droplets with deferent sizes (FIG. 2d, Fig. e-g). Droplets of 80 μm in diameter are first flowed into the channel (height: 500 um) and trapped in the microwells until all the microwells are filled (FIG. 4a). Droplets of 40 μm in diameter are then sorted, trapped and one-to-one paired to the 80 μm droplets in the microwells (FIG. 4b). After flushing out the excess of untrapped droplets, an oil containing 2% (v/v) perfluoro-butanol (PFO) is flowed into the device channel as a demulsifier to trigger merging events (FIG. 4c). Subsequently, an oil with 2% EA surfactant is flowed into the device channel again to re-stabilize the merged droplets, which are then being released from the microwells by flipping the device (FIG. 4d). The droplet capturing and merging efficiencies of our device were characterized by two color droplets containing a red or green food dye for visualization (FIG. 4e). The co-encapsulation experiment employs Hela cells stained with a blue florescent dye (nuclei-blue, thermal fisher) and 30 um micro-beads (TOYOPEARL HW-65S) were suspended in PBS solution with 16% (v/v) OptiPrep density gradient medium (Sigma) to avoid cell aggregation.

Results and Discussion

Serially Generating and Sorting Two Different Sizes of Droplets that Contain Two Particle Species Hydrodynamic trapping in a microfluidic device has been widely used for single-cell capturing (21). However, the heterogeneity of cell types exhibiting size variations makes the size-based capturing mechanism of hydrodynamic trapping unsuitable for heterogenous biological samples. Alternatively, a flow-focusing structure (22) can encapsulate single cells in mono-disperse micro-droplets of uniform size, providing an ideal means to capture single cells in heterogeneous sizes. This approach first requires generation of droplets in a constant size that is large enough to encapsulate all cells yet fits to capturing chambers. Although many other studies elucidated the mechanism of droplet formation, there exists no simple scaling law for generating a desired droplet size due to many dimensional and fluidic parameters to be considered (23). The height (h) and width (w) at the orifice of the flow-focusing region of the device are the most important parameters controlling the size of droplets. There are two design criteria to be considered. First, the channel size needs to be large enough to avoid mechanically lysing cells in the chamber or clogging the microfluidic chamber. Second, the droplet size should, in general, be as small as possible to maximize the assay throughput while maintaining its monodispersity. Therefore, the optimized device design should, in general, incorporate an orifice whose size is slightly smaller than the desired droplet size and larger than the cell or bead.

Figure 3:
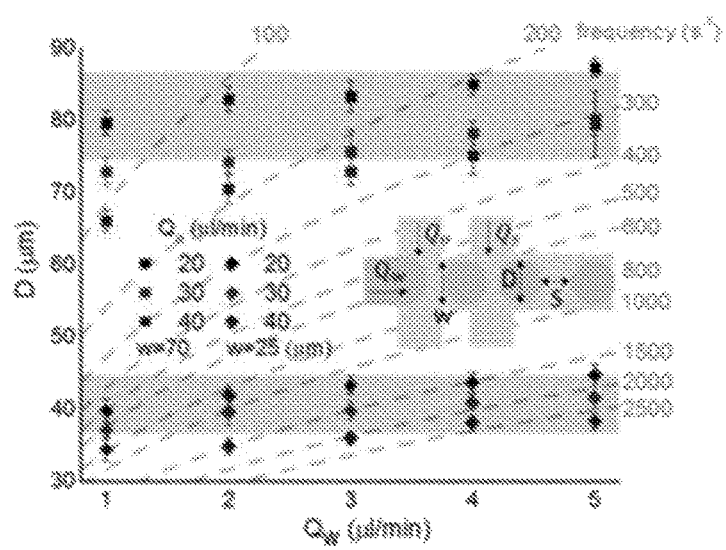
FIG. 3. Diameter D (μm) and throughput ($s^{-1}$) of generated droplet under different original oil ($Q_o$) water ($Q_w$), and spacing oil ($Q_s$) flow rates (μl/min). Devices with two different orifice features (25 μm×40 μm and 70 μm×70 μm) are used to generate droplets with 40+/−4 μm and 80+/−8 um dimeters. $Q_s$ is set to guarantee a minimum distance S~12*D between two adjacent droplets. Therefore, $Q_s=(S \cdot Q_w)-Q_o$.
Figure 3:
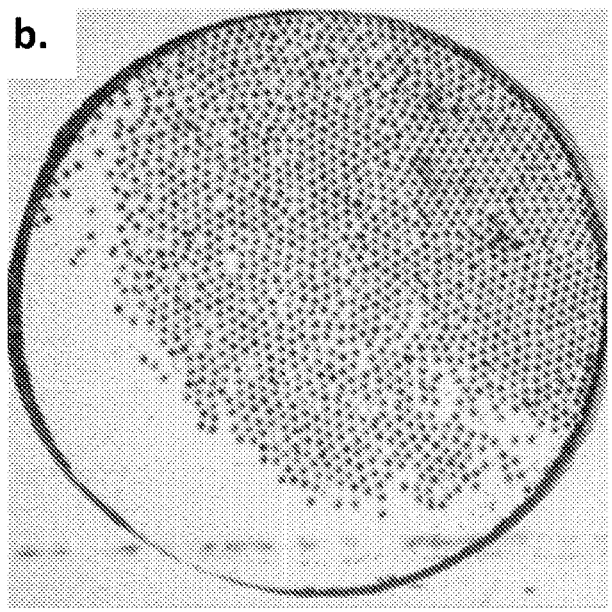
Figure 3:
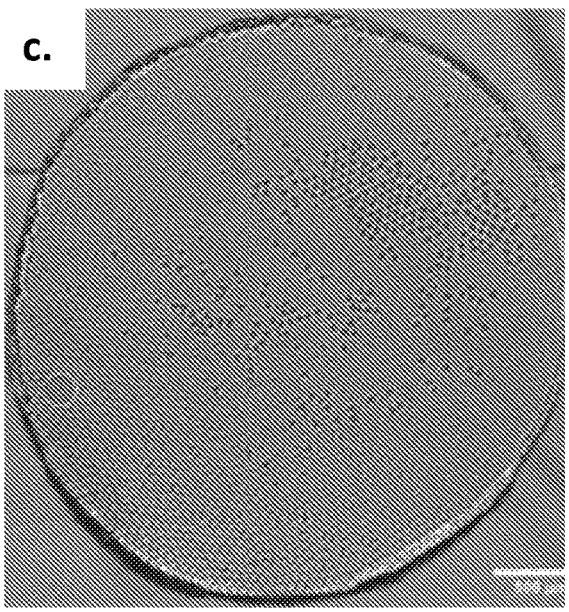

Two different device designs were explored that generate 40 μm- and 80 μm-diameter droplets, which are capable of encapsulating most of the mammal cells or engineered microbeads (<60 μm), respectively, at highest throughput. FIG. 3 shows the formation of different droplet sizes resulting from different combinations of water and oil flow rates (Qw and Qo). By adjusting the water/oil flow rate ratio, both devices met design specificity (shaded zone). After generation, the droplets were flowed through a short channel for stabilizing the interface, and a spacing oil was added to provide a proper distance between each droplet. The presence of a droplet itself generates additional hydraulic resistance against other droplets flowing within the channel. Thus, generating enough spacing between two adjacent droplets is important as it prevents physical interferences between droplets at the Y-shaped outlet junction. The optimal spacing distance was achieved by adjusting the oil-to-water flow ratio until all the droplets flowed into the collection channel or the waste channel at the presence, or absence of the electric field, respectively. Here, the flow rate of spacing oil Qs is given by $Qs=(S \cdot Qw)-Qo$, where $S=12$ represents the droplet-to-droplet distance normalized by the droplet diameter, which is approximately equal to the disperse phase-to-continuous phase volume ratio. It was found that the applied electric field was not able to reliably deflect every droplet into the collection channel when the water flow rate exceeds 5 μl/min. For this example, this generally sets the upper bound for the sorting throughput at 2000 s$^{-1}$ for 40 μm droplets and 300 s$^{-1}$ for 80 μm droplets, respectively.

Figure 7A:
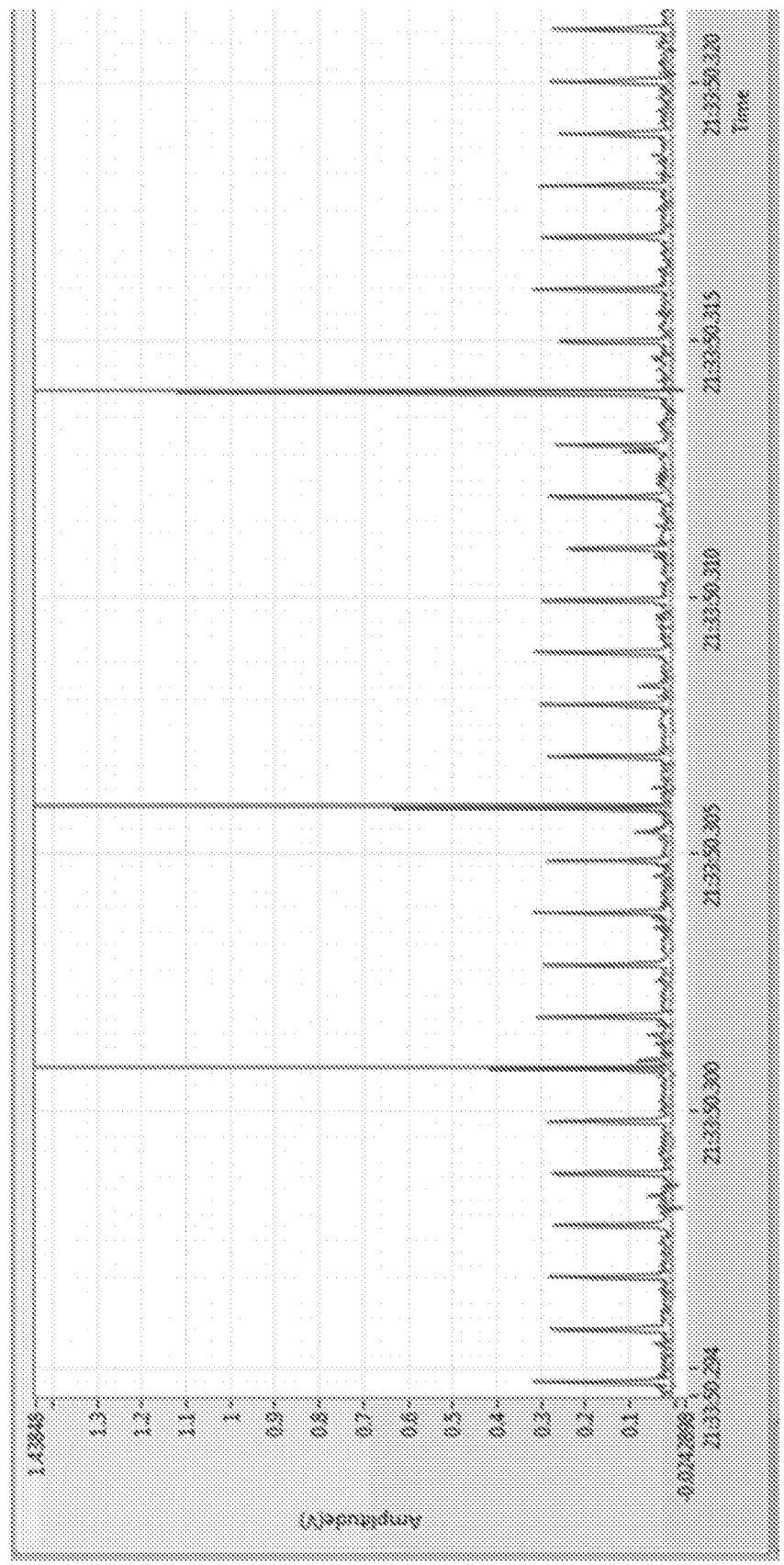
FIGS. 7A-B show scattering signal detected from empty droplets and droplets contain cells. Lighter lines indicate that cell sorting events can be triggered without fluorescent labeling. This may also be used to sort out larger cells (e.g. circulating cancer cells) from smaller cells (e.g. red blood cells) from a sample that contains mixed cell populations (e.g. blood).
Figure 7B:
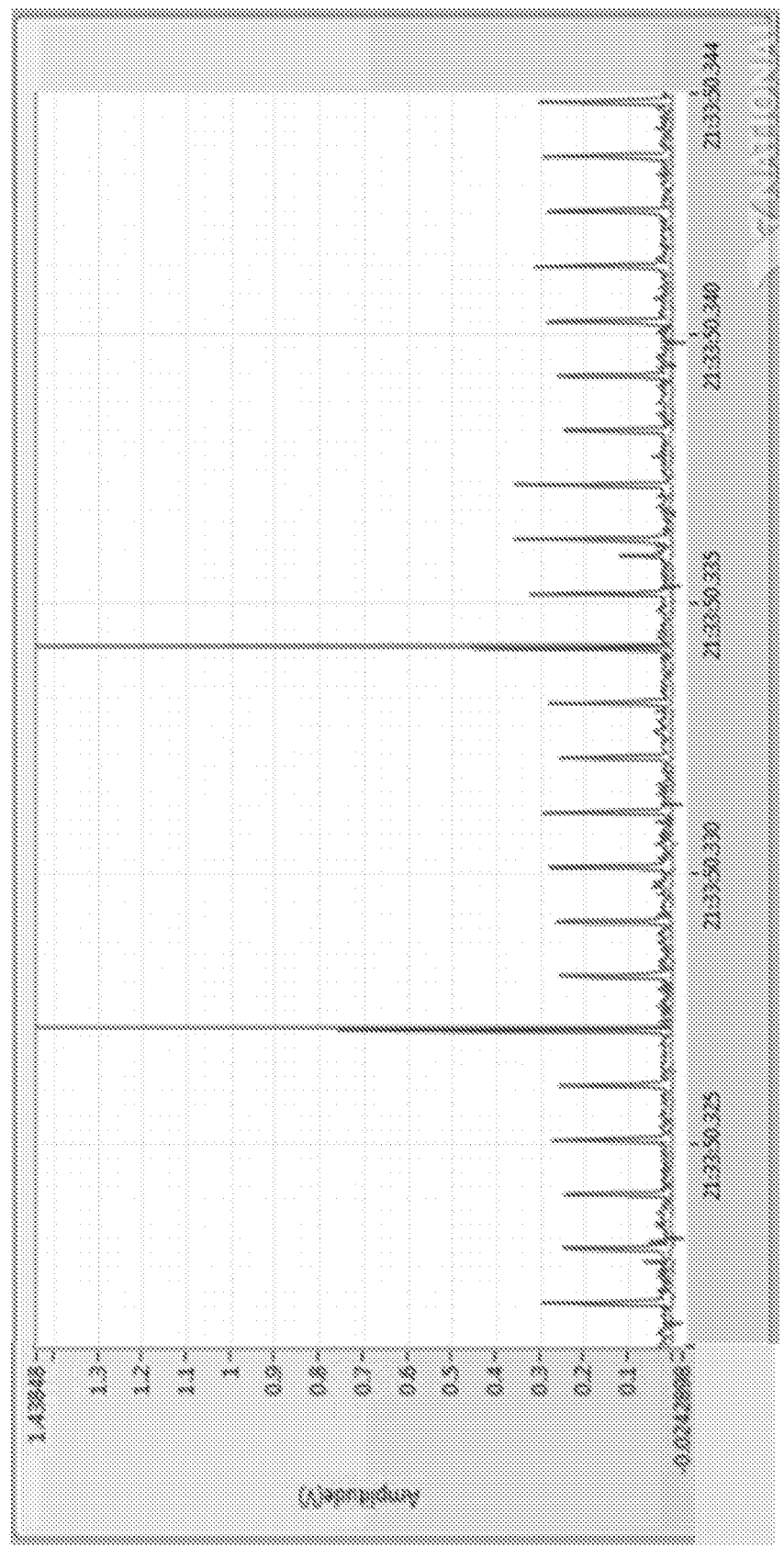

We next validated the accuracy of the droplet generating/sorting device performance by using fluorescently labeled Hela cells and non-fluorescent microbeads. The validation process started with generating 40 μm single-cell containing droplets and 80 μm single-bead droplets with a suspension of 1,500 cells/μl and 180-200 beads/μl, respectively. Such concentrations correspond to 0.05 cell per 40 μm droplet (a=0.05), and 0.05 bead per 80 μm droplet (λb=0.05), respectively. The sorting operation of the device was subsequently performed and resulted in more than 98% of sorted droplets containing at least a single cell or bead with empty droplets discarded (FIG. 3b-c). We observed that a small (<2.5%) population of sorted droplets contained a doublet or clumps which could not be easily excluded from the sorting process. But the generation of these bad droplets could be minimized by further diluting the sample concentration or by pre-filtering step to remove clumps. Both the signal-to-noise ratio (SNR) and the setting of sorting gates determined the rate of false negative outputs. False negative droplets contain either cells or beads but not being sorted. We suppressed the false negative output rate down to <1% by applying an appropriate sorting gate (FIG. 6). Sorting cells based on scattering light also worked but resulted in a higher false negative output rate due to the small SNR of the weak signal (FIG. 7).

Droplets Capturing, Paring, and Merging

The technical challenge to efficiently merge two droplets with one-to-one precision is significant. This example describes a strategy, in which the droplets are generated and sorted serially to overcome the problem of synchronizing the two droplets. In this example, the inlet of the merging device is directly connected to the collection outlet of the droplet generating/sorting device via a microbore tubing. The on-chip operation guarantees no-loss droplet transfer while preventing them from being destroyed by surface tension force that emerges during off-chip operation. The droplet merging device also requires exerting no significant backpressure to the droplet generating/sorting device, therefore not interfering the flow speed originating from the droplet generating/sorting device. Meeting these requirements would be difficult with a conventional droplet merging technique driven by a hydrodynamic pressure gradient along the flow direction. Instead, in this example, we employed an approach of utilizing buoyancy that generates vertical trapping force orthogonal to the flow direction. This feature also allowed us, for example, to do "hot-swapping" of the filled merging device without disrupting the independent sorting function.

Another challenge that we addressed was to achieve a high droplet retention rate, which is given by the ratio of the number of captured droplets to the number of input droplets. Most of conventional droplet merging experiments requires abundant droplets to guarantee filling of nearly all capturing sites. While this leads to a high occupancy rate, a large proportion of droplets are wasted resulting in a significantly low retention rate. In contrast, our post-sorting/alignment strategy can retain very small number of droplets in the merging sites to achieve both high retention and high trapping site occupancy rates at the same time.

FIG. 4a-d shows the side views of the merging device and the workflow of merging pairs of 80 μm-diameter green (larger) droplets and 40 μm-diameter red (smaller) droplets. The device chip has 1,152 trapping sites, each of which is composed of a larger microwell and smaller microwell to trap the 80 μm- and 40 μm-diameter droplets, respectively. We first flowed green-dyed large droplets into the device, where its large-dimension flow channel slowed down the flow speed and allowed the introduced droplets to be stagnant, moving slowly along the top side of the channel. Once a desired number (detailed below) of the green droplets were collected, we turned off the upstream sorting operation and disconnected the tubing from the droplet sorting device. Then, the droplets were floated into the empty trapping sites by tilting the merging device and consequently trapped inside the larger microwells. This operation is performed under an optical microscope to allow better tilting control and visual confirmation that all the droplets are gradually filled in the trapping sites. By carefully control the tilting direction, angle, speed and magnitude of the device, we can apply proper buoyance force within the merging device to achieve both high occupancy and retention rates. We found that nearly 100% retention rates can be achieved when the number of input droplets were smaller than the on-chip trapping sites (1,152 wells/chip) (FIG. 4e, squares). A nearly a 100% occupancy rate could also be achieved by loading as few as 1200 droplets into the device (FIG. 4e, squares). Once all the larger microwells were filled with 80 μm-diameter droplets, we introduced an external oil flow to wash out uncaptured excess droplets. The captured droplets stably remained in the capturing-sites during the washing process at a flow speed<10 mm/sec.

Next, we flowed the smaller 40 μm-diameter droplets into the merging device to fill the smaller microwells adjacent to the larger ones previously captured larger 80 μm-diameter droplets in a similar operation (FIG. 4b). Once all the trapping sites are filled with droplet pairs, we again introduced an external oil flow to wash out the excess droplets. We can achieve close to 100% retention and pairing rate when fewer than 400 smaller droplets are flowed into the device, while this rate drops to ~80% when the total input increases to 800 (FIG. 4e, triangles). To be noted is that, in this particular Example, it requires flowing in ~2000 smaller droplets to achieve an occupancy rate of 87%; and the retention rate decreases to 50% (FIG. 4e, triangles). The overall less efficient capturing rates for the smaller 40 μm-diameter droplets can be explained by the fact that the droplets with the smaller size has less chance to flow through the smaller microwells. Meanwhile, the smaller droplets experience relatively stronger drag force, which slows down their motion. Finally, an external oil containing 5% PFO was flowed into the device to destabilize and merge two adjacent droplets (FIG. 4c). The PFO molecule presenting at the interface between the two types of droplets increases the surface tension. The additional pressure provided by the oil flow generates physical contact between the two droplets, which triggers the merging events. Only a very small fraction of the droplet pairs did not merge (typically <1%) because the 40 um-diameter droplets became wetted to the PDMS channel surface before contacting with 80 um-diameter droplets. After re-stabilized with EA surfactant, the merged droplets were released from the capturing-sites by flipping the device chip. (FIG. 4d).

Single-Cell and Microbead Co-Encapsulation

Figure 5:
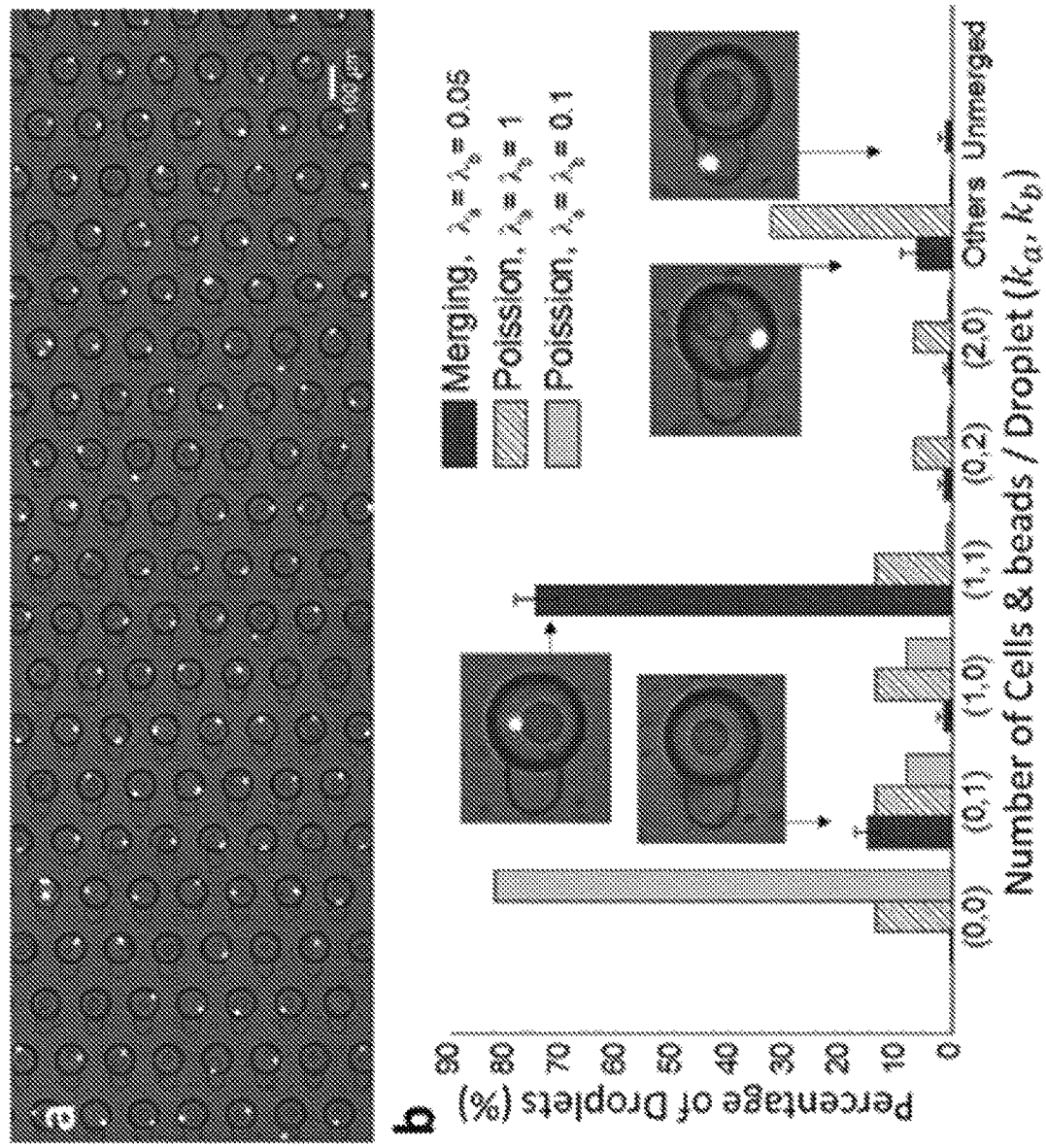
FIG. 5a shows a scanned image of merged droplets in an exemplary droplet merging device. Florescent Hela cells and microbeads are co-encapsulated one-to-one in each droplet.
FIG. 5b shows a histogram that shows the percentage of droplets that contain the numbers of cells (ka) and beads (kb). The estimated co-encapsulation resulting from the co-flow method is also plotted based on Poisson statistics with $\lambda a=\lambda b=1$ or 0.1. Five sets of experiments were repeated. (Average number of droplets for each test=1080).
Figure 6A:
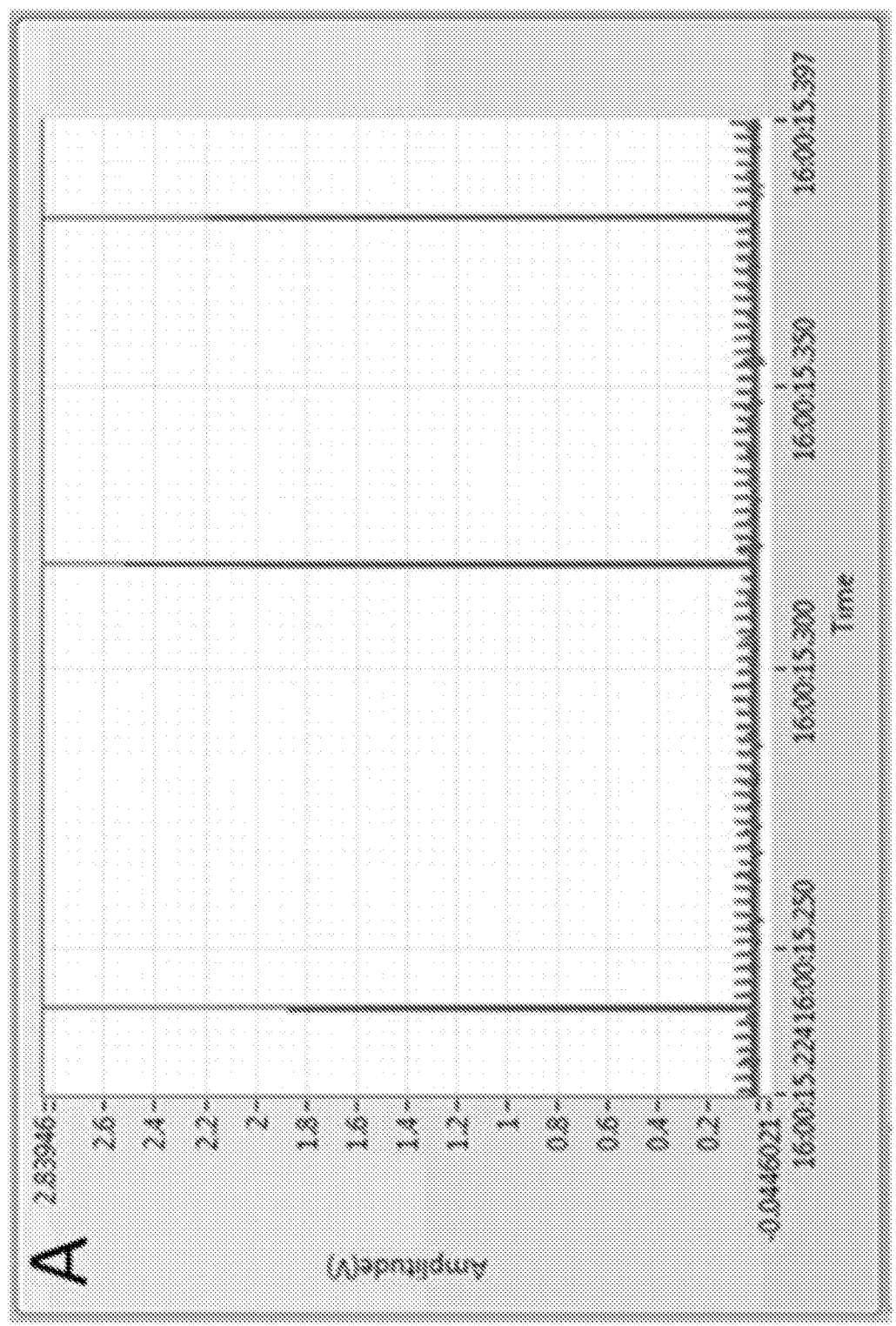
FIG. 6A shows a time sequence of scattering light signals (darker lines) detected from empty droplets (peak value ~0.1V) and droplets containing beads. The lighter lines indicate the TTL signal which triggers the sorting events. The x-axis represents system clock readings (hours: minutes: seconds. milliseconds).
Figure 6B:
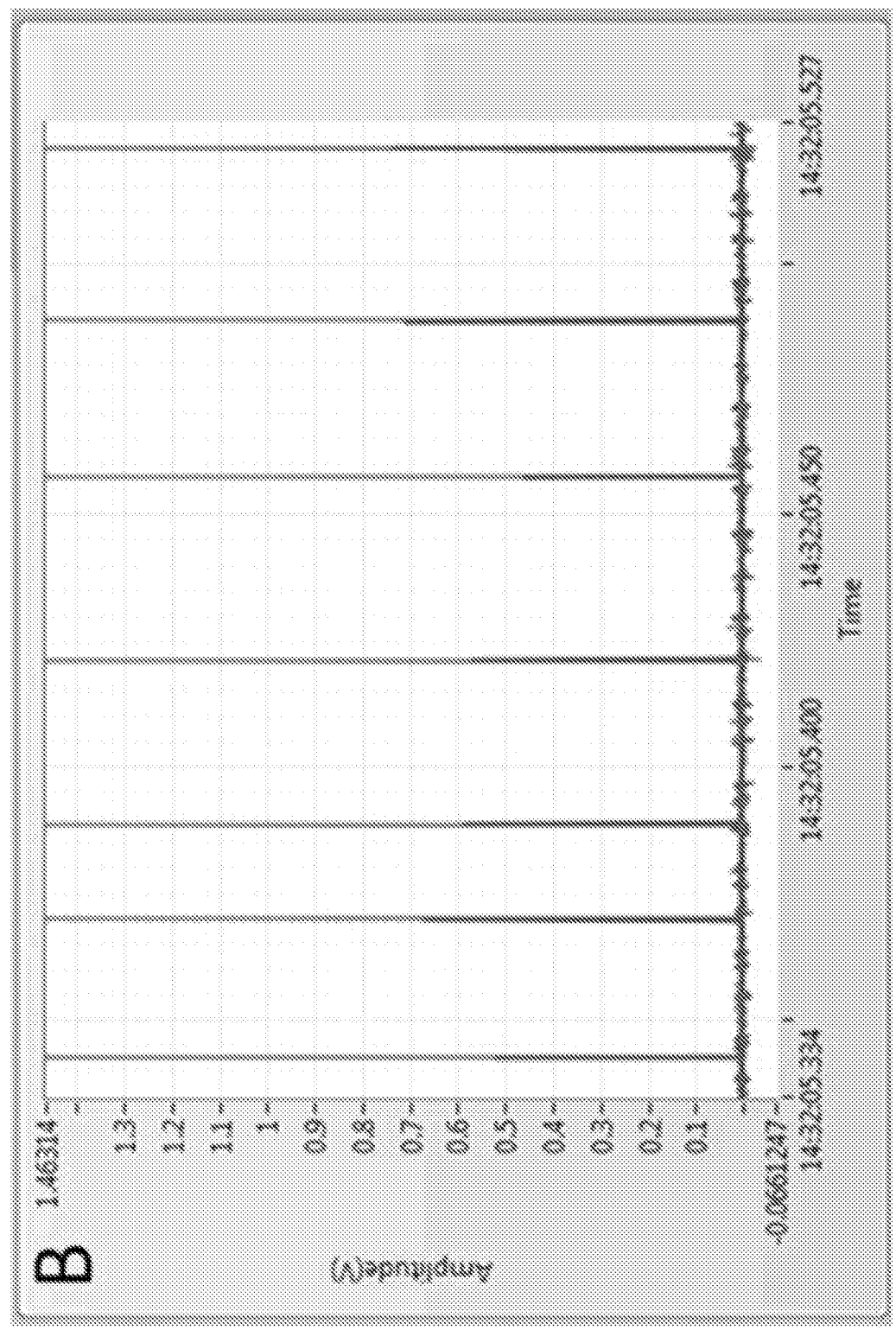
FIG. 6B shows fluorescence signals detected from droplets containing cells. The empty droplets contain no fluorescent molecules, therefore, cannot be detected.
Figure 6C:
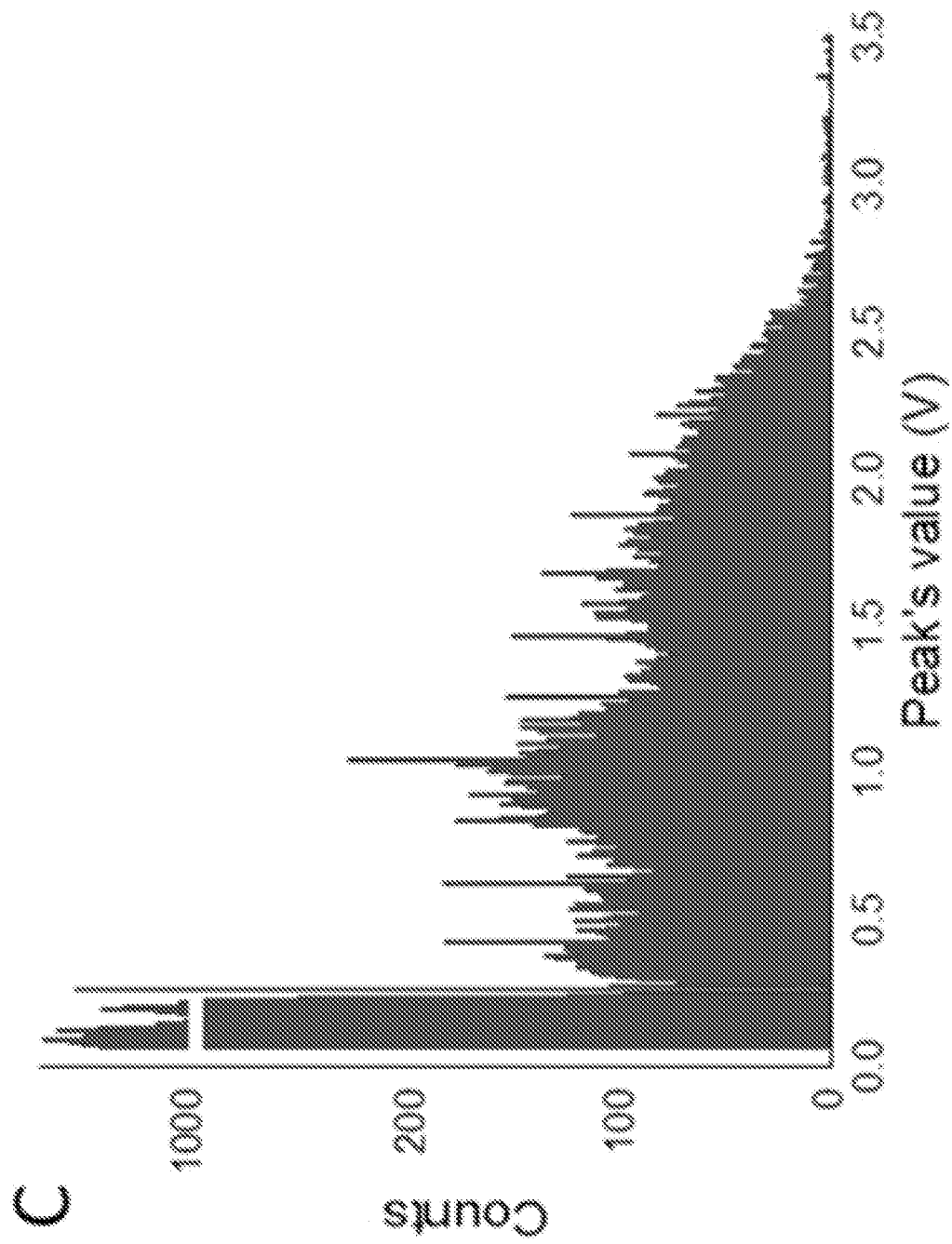
FIGS. 6C and 6D Histograms of detected peak values for beads (C) and cells (D) extracted from (A) and (B). The lighter line indicates the sorting gate value.
Figure 6D:
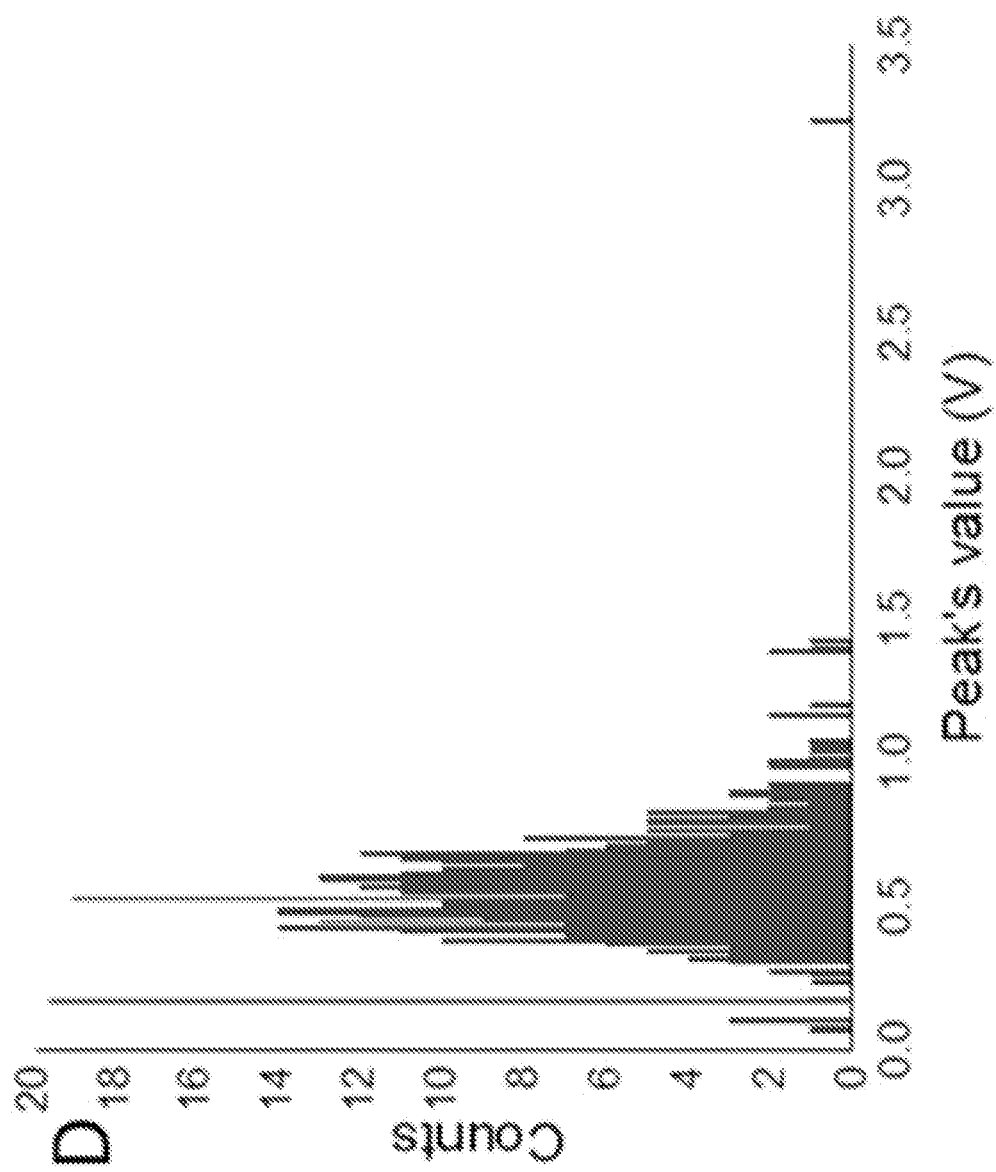

Using the same system mentioned above, we sequentially sorted 1,300 bead-containing (80 μm-diameter) droplets and 2,000 fluorescent cell-containing (40 μm-diameter) droplets into the merging device with an array of 1152 trapping sites. Nearly 100% of the trapping-sites were filled with bead-containing droplets, and 85% of theses droplets were paired with subsequently trapped cell-containing droplets. After merging all the droplet pairs, we counted the number of cells and beads in each droplet. FIG. 5 shows the optical image of the merged droplets on the device (FIG. 5a) and plots the fractions of the droplets containing ka cells and kb beads across the total counted droplets of N=5,400 from 5 devices (FIG. 5b). We found that 74.5% of the droplets exactly encapsulated a pair of one bead and one cell. Another 15% of the droplets contained only one bead due to a failure in droplet pairing before merging. Another 7.9% of the droplets encapsulated multiple beads and/or cells such that (ka, kb)=(0, 2), (2, 0), (1, 2), (2, 1), . . . as a result of a doublet of cells or beads existing in some of the sorted droplets. And the rest contain empty or unmerged droplets. In general, the probability of achieving the one-to-one paring of a single bead and a single cell in a merged droplet using the device in this Example using the above conditions is given by:

$$P(k_a=1 \cap k_b=1,_{merging}) = \eta * P_{\lambda_a}(k_a=1|k_a \geq 1,_{poission}) * P_{\lambda_b}(k_b=1|k_b \geq 1,_{poission}) \quad (2).$$

where η is the occupancy of the 40 μm-diameter droplets in the merging array defined in FIG. 5e. $P_\lambda(k_a=1|k_a \geq 1$, poission) is the probability of generating sorted droplets that contain single cells and $P_{\lambda,b}(k_b=1|k_b \geq 1$, poission) is the probability of generating sorted droplets that contain single beads. FIG. 5b also shows the co-encapsulation result expected for the conventional scheme, which is simply given by multiplying two independent Poisson statistics fractions as:

$$P_{\lambda_a,\lambda_b}(k_a,k_b,_{poission}) = P_{\lambda_a}(k_a,_{poission}) * P_{\lambda_b}(k_b,_{poission}) \quad (3).$$

At a concentration of one cell/bead per droplet resulting in $\lambda_a=\lambda_b=1$, the one-to-one pairing rate reaches a maximum rate such that $P_{1,1}(k_a=k_b=1,_{poission})=13.5\%$. However, there is a high fraction (32%) of droplets that contain multiple cells/beads. Such a population is even 2.4-fold larger than the desired population of droplets with an exact pair of one cell and one bead. Minimizing the percentage of droplets containing more than a single paired particles is important in practical droplet-based assays. For example, Drop-seq assay requires one-to-one paring between a cell and a bead engineered with unique ssDNA barcodes. If such a bead was paired with more than a single cell, it could capture mRNA molecules from multiple cells. The resulting cDNA from the different cells will be tagged with the same barcodes and recognized as the cDNA from the same cell. Therefore, the transcriptomic information extracted from this particular bead becomes incorrect and leads to a wrong data interpretation. To avoid this, the conventional Drop-seq assay uses a low concentration of cells (beads), which is equivalent to ~one cells (beads) per 10 droplets ($\lambda_a=\lambda_b=0.1$). Governed by the Poission statistics, the assay needs to dilute the sample as much as 90% of cells (beads) become wasted to reduce error (i.e., the probability of incorrect cell-bead pairing down to 0.136). In contrast, our approach with the active sorting and downstream merging achieves as high as cell-bead pairing accuracy resulting in an error as small as 0.083 without increasing the sample loss of 15% and 50% for beads and cells, respectively. Indeed, the loss remains constant as it is solely determined by the droplet merging device design, not by the Poission statistics. As a result, such accuracy can be further enhanced by reducing the sample concentration in the method without affecting the sample loss.

This example describes a microfluidic system that couples droplet sorting and merging to achieve one-to-one pairing of two distinct particles inside droplets. This methodology eliminated the significant sample loss resulting from a conventional co-flow setup governed by the Poission statistics. The particles were actively captured and paired in the sorting and merging devices without involving a stochastically process. The resulting one-to-one pairing efficiency in this Example reached 74.4%, which represents a significant improvement in both pairing accuracy and yield as compared to the conventional Poission distribution-limited paring efficiency of 13.5%. We found that it was the droplet retention rate determined by the device design, not the Poission statistics, that dominated the sample loss. This Example demonstrates a versatile droplet manipulation sequence including passive encapsulation, opto-activated soring, stop-flow capturing, size-selective pairing, and on-demand merging in a highly-integrated platform. The developed platform imposes no restrictions on the physical properties (size, shape, stiffness . . . etc.) of particles as long as they can be optically differentiated. The system shows the ability to perform assays with a wide range of sample density. The number of the microwells in the droplet merging device is also scalable from tens to thousands, or more, due to its simple design. Furthermore, the system enables in-device examination before and after droplet merging, which allows direct measurement of pairing quality and direct observation of reactions after merging, respectively. The versatility of the system makes it suitable for a wide spectrum of assays. For example, it can be applied for studying cell-cell interaction between two distinct cell types or single-cell transcriptomic/proteomic analysis by using primers/antibody-coated microbeads.

Example 2

Single Cell Transcriptome Profiling

This Example describes systems and methods for high-throughput and high-recovery mRNA sequencing for single cells.
Methods
This Example utilizes the same Microfluidic system, Droplet generating/sorting device and Droplet merging device as Example 1 does to one-to-one merge primer containing droplets and single cell containing droplets. This droplet pairing-merging method has the benefit of being more cost effective as it saves lots of costly reverse transcription reagents. For instance, it uses as little as 5 uL of reverse transcription reagents to generate 80 um droplets for multiple merging devices. To run the same sample size, it takes at least 10 times reverse transcription reagents for experiments like "drop-seq" and "in-drop."

To profile mRNA information from single cells, UMI and barcode containing reverse transcription primers are used to copy mRNA into DNA sequences and subsequently amplified by poly chain reaction (PCR) for next generation sequencing. Each primer is composed of, from 5'-terminus to 3'-terminus, a PCR specific sequence, a 12-mer UMI sequence, a spacer sequence, a 20-mer barcode and a 25-mer poly-dT. Primers in the same droplet contain unique UMIs and the same barcode to uniquely identify each mRNA molecule while tagging all the mRNA molecules from the same cell (i.e. in the same droplet) by the same barcode. 80 μm primer containing droplets will first be generated and sorted into the merging device. Subsequently 40 μm single cell containing droplets will be generated and sorted to one-to-one pair and merged with the 80 μm primer containing droplets for subsequent cell lysing and mRNA copying.
Generation of Primer Containing Droplets One way to generate primer containing droplets is to encapsulate reverse transcription primer-conjugated microbeads into 80 μm droplets. The primer-conjugated microbeads can be obtained as described in the "drop-seq" (6) and "in-drop" (16) papers.

A second way is to PCR-amplify primers in droplets for highly efficient priming and gene recovery. The PCR step is important because it overcomes two major limitations of using primer-bead: 1) it provides many fold higher concentration of reverse transcription primer for the reverse transcription, and 2) it transforms the reverse transcription into solution, which eliminated the space limitation on the bead for priming mRNAs and increases priming efficiency because short primers are more freely diffusing to hybridize onto the much larger mRNA molecules. In brief, 80 μm droplets are generated in the same way to include a PCR template-conjugated microbead in each droplet, encapsulated with regular PCR reaction solution with a amplifying primer. The single stranded DNA templates on the microbead contain, from 5'-terminus to 3'-terminus, a 30-mer poly-dA sequence, a 20-mer barcode and a 25-mer spacer. Each of the amplifying primer contains, from 5'-terminus to 3'-terminus, a PCR handle sequence, a unique random 12-mer UMI and a 25-mer sequence that is reverse complement to the spacer of the template. After encapsulating and sorting the template-microbead containing droplets into a merging device, PCR reaction is performed in a commercial thermal cycler via using an adapter to linearly amplify the reverse complement sequence of the template from each microbead. The amplified single stranded DNA molecules become freely diffusive mRNA reverse transcription primers, each of which contains from 5'-terminus to 3'-terminus, a PCR handle sequence, a unique random 12-mer UMI, a 25-mer spacer sequence, a 20-mer barcode, and a ~30-mer poly-dT sequence.
Reverse Transcription and Next Generation Sequencing Library Amplification For experiments that utilize 80 μm droplets that contain reverse transcription primer-conjugated microbeads, cell-containing 40 μm droplets are merged as described in Example 1. As the 80 μm droplets also contain lysis buffer and reverse transcription reagents, the cells are lysed after merging. Subsequent reverse transcription reaction and next generation sequencing library amplification can be found in the "drop-seq" (6) and "in-drop" (16) papers.

For experiments that utilize primer-amplified droplets, two sequential merging events by electricity are employed (see, FIG. 8). The 80 µm primer-amplified droplets will first be merged with 40 µm droplets that contain lysis buffer and reverse transcription reagents to generate the equivalent 80 µm droplets as mentioned above. As droplet size only changes to ~83 µm after the first merging event, 40 µm cell-containing droplets can be merged again for cell lysis and subsequent reverse transcription and sequencing library amplification, similar to those described in the "in-drop" paper (16), and commercialized SMART-seq2 protocol.

Example 3

Single Cell mRNA Sequencing with Highly Efficient Cell Recovery and mRNA Recovery This example employs the electric multi-well type array as shown in FIG. 8. This device sequentially performs cell lysis and subsequent biochemical and enzymatic reactions all inside the droplet. In general, we first generate approximately 130 µm-diameter droplets, containing biochemical and/or enzymatic reagents and sort them into the paring-merging device to fill all the larger wells. Next, we generate approximately 60 µm-diameter cell lysis droplets into the same paring-merging device by co-flowing cell suspension with lysis buffer that contains 2× concentration of detergent. The type of device from FIG. 8 controls the sheer flow that separates the cell suspension and lysis buffer until the two aqueous phases are co-encapsulated in the same droplet. As it requires some time to diffuse and mix the two aqueous phases, cells are not lysed right after droplet formation at the detection and sorting position. Indeed, it was observed that cells, including their nuclear envelopes, were only completely lysed in about 20 seconds after sorted into the pairing-merging device. As the volume of the chemical/enzymatic reagent-containing droplet is ~10× of that of the cell lysis droplet, detergent concentration is ~11× diluted after droplet fusion and its inhibitory effects is eliminated. However, since the diameter of the fused droplet only increases by ~3%, it remains securely in the larger well for subsequent rounds of fusions.

Figure 13:
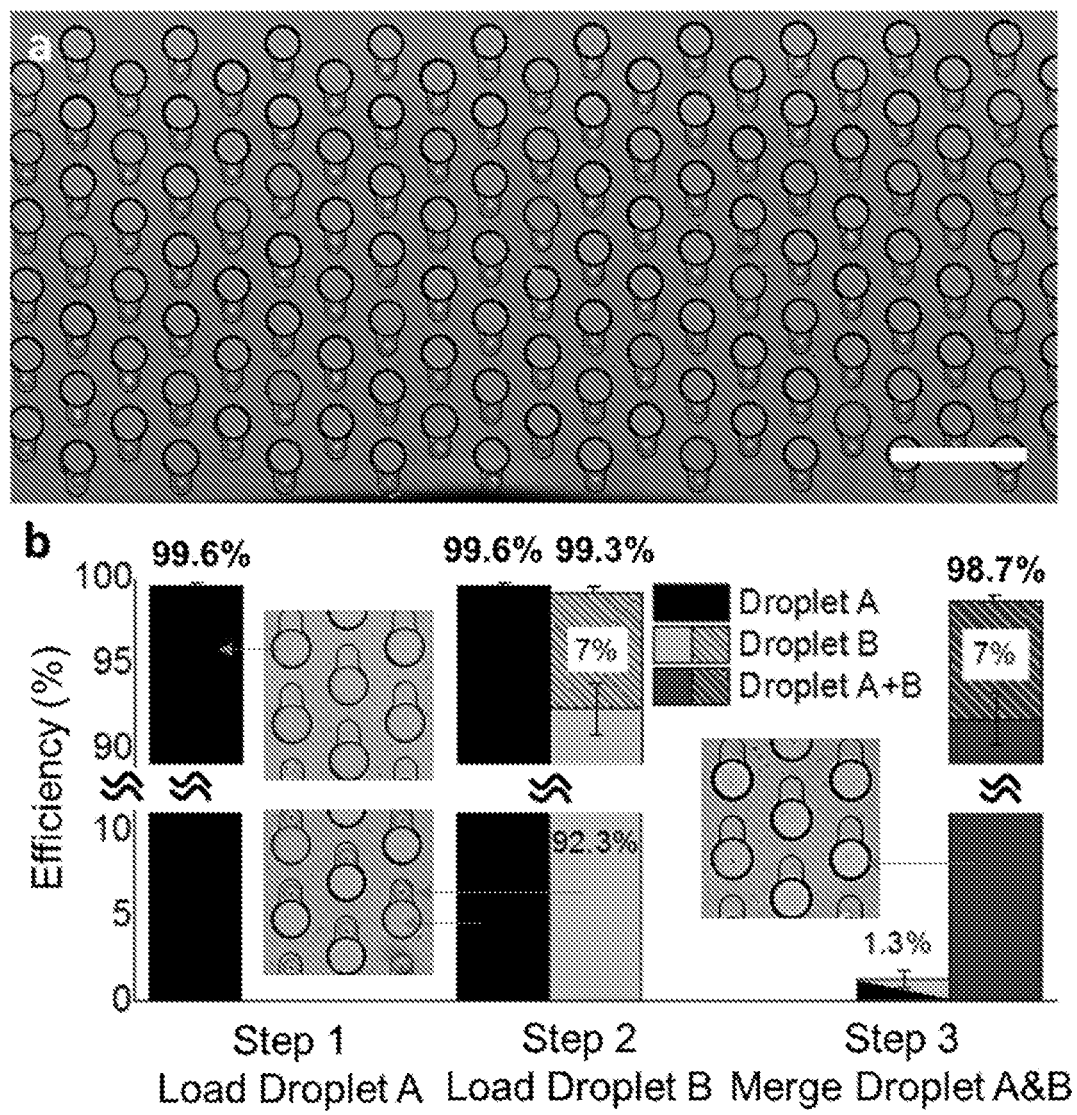
FIG. 13 shows quantification of the merging device efficiencies from Example 4. (a) Image of paired droplets in droplet storage array. The dashed circles indicate there are multiple cells in droplet B. (b) Efficiencies for droplet trapping, pairing, and merging. The slash bars indicate the droplets containing more than one cell.

We first sort the large droplets into the pairing-merging device by co-flowing reverse transcription reagents with barcoded mRNA-capturing microbeads to fill each of the reaction wells. Small droplets containing single cells are then generated, sorted, one-to-one paired and merged with the large droplets as described above. The use of the 60 µm diameter droplets, as opposed to smaller ones, makes it easier to capture them in the pairing wells due to the larger buoyancy force generated by the larger volume, therefore cell recovery rate is >98% under most of the filling conditions (FIG. 13). Secondly, electricity based fusion has certain advantages compared to using surfactant, which can decrease the stability of the two paired droplets, which somehow causes aqueous solution in the fused droplet much easier to diffuse out from the droplet. This can be difficult when performing in-droplet reverse transcription at the optimal temperature, such as 50° C. As the electric based type device of FIG. 8 uses dielectric force to fuse two droplets, the fused droplets remain very stable. The size of the fused droplets has ignorable change after 30 minutes of in-droplet reverse transcription incubation at 50° C., indicating there is minimal aqueous diffusion or evaporation. We hypothesize that in-droplet mRNA reverse transcription is highly efficient as the substrates are highly concentrated in a much smaller volume than in the bulk reaction. Indeed, we found that combined with the advantage of 2× detergent cell lysing, this protocol can detect the same genes per cell using less than 2-fold of total sequencing reads when comparing to other droplet based single cell sequencing platforms, which is compatible to that of SCRB-Seq, a low cell throughput platform that has been used as the best mRNA recovery performance of all unique molecular identifier enabled scRNAseq technologies [FIG. 3 in (Ziegenhain et al., 2017, Mol Cell 65:631-643)]. In-droplet reverse transcription also completely avoids gene detection contamination between different cells that happens in bulk reaction used by all other droplet-based platforms.

Example 4

Single-Cell mRNA Detection

This Example describes a hybrid platform that integrates continuously droplet sorting and stationary droplet merging which gets rid of off-chip and on-chip droplets transition. This approach enables additive merging of two or more distinct types of droplets in a stationary array format. By sequentially adding lysis buffer and RT-LAMP (revers transcription loop-mediated-isothermal amplification) mixture into single-cell reactors, we demonstrated a simple and rapid mRNA detection technique that enables one to differentiate different cell types by their gene expressions. The fully on-chip workflow including cell isolation, sorting, lysing, and RNA detection provides a robust experimental pipeline for a wide variety of single-cell analysis.

Workflow of Single-Cell RT-LAMP Assay Using Sort N Merge Platform

Figure 11:
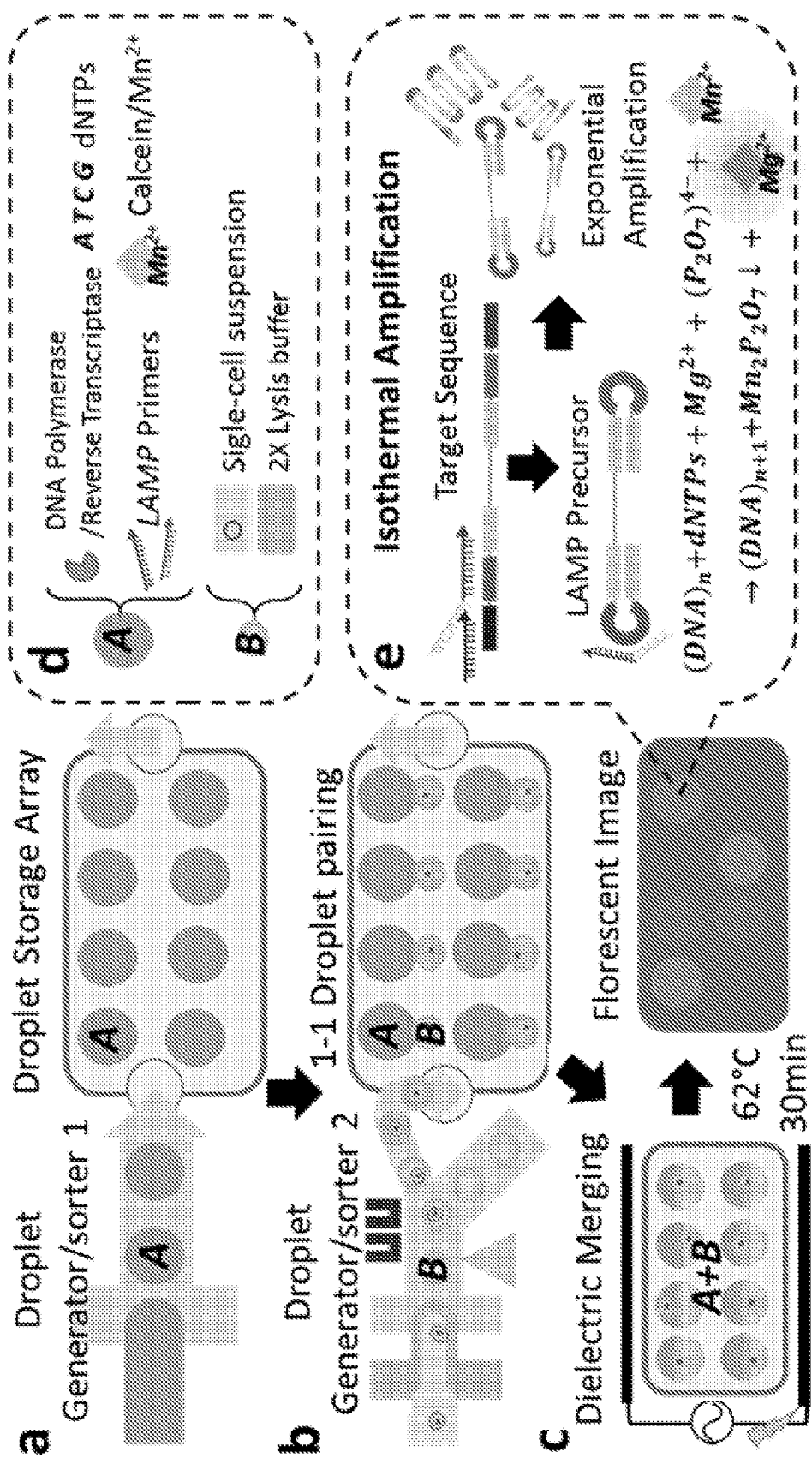
FIG. 11 shows schematics of single-cell RT-LAMP assay using a Sort N' merge platform from Example 4. (a) Droplets containing LAMP reagents (Droplet A) are first generated by droplet generator 1 and stored in the merging device. (b) Droplets containing single-cell and lysis buffer (Droplet B) are generated and sorted into the merging device. Droplet A and Droplet B are anchored and paired by buoyancy and the physical trap. (c) The paired droplets are merged by electrohydrodynamic force. RT-LAMP reaction is performed at 62° C. for 30 min followed by image-based fluorescent measurement. (d) The components of the droplets. (e) Principle of RT-LAMP reactions.

There were two important steps in Sc-RT-LAMP assay: cell lysis and RT-LAMP reaction, which were performed separately in droplets A and B (FIG. 11). The droplet A containing LAMP reactant mixture, fluorescent dye, and metal quencher were first generated by flow-focusing structure and collected into the merging devices (FIG. 11a,d). The merging device was composed with a large flow channel and an array of microwell chambers on top of it. The geometry of microwells was designed to fit only two droplets with different sizes (Droplet A: 130 um, Droplet B: 60 um). This enable each microwell chamber to store a couple of droplets with physical contacts. The droplets with reactant mixture can be spread through the flow channel by tiling the device and float into the microwell chamber. Those uncaptured droplets remaining in the flow channel can be washed by applying an additional oil flow.

Figure 12:
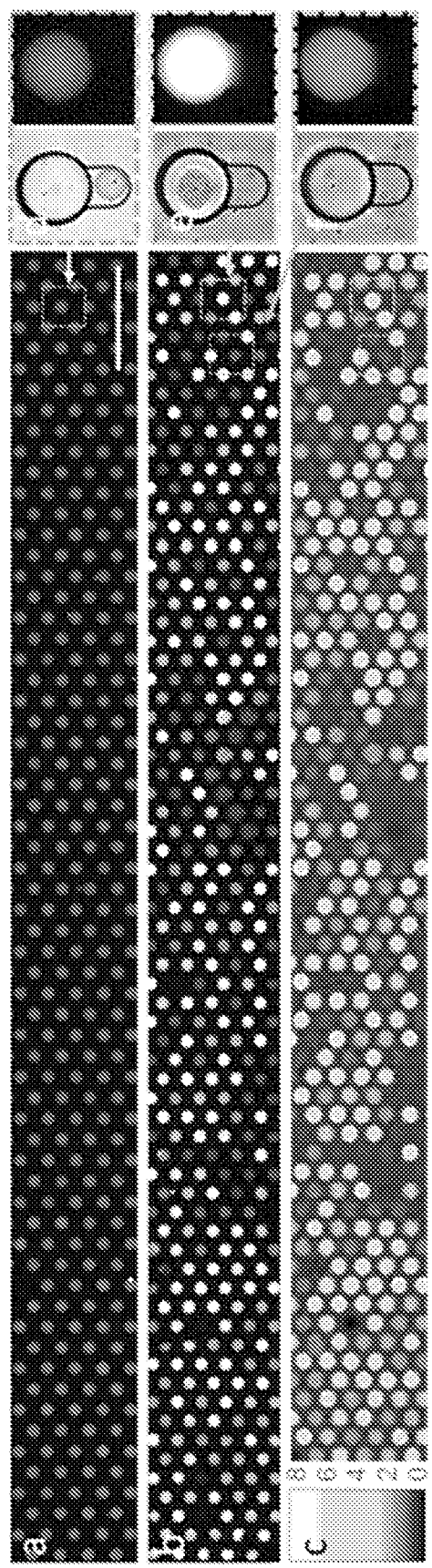
FIG. 12 shows visualization of two-step RT-LAMP in the sort N' merge device from Example 4. Florescent images of droplets before (a) and after (b) RT-LAMP reaction. (c) The normalized intensity changes (I_b−I_a)/I_a before and after RT-LAMP reaction. Magnified transmit light and fluorescent images show a merging well with a cell-containing droplet before merging (d) and after merging/RT-LAMP reaction (e), respectively. The same images for a merging well with no RT-LAMP reaction after merging (f).

Next, the droplets containing cells and buffers were generated by co-flowing single-cell suspension and lysis/PBS buffer (FIG. 11b). To differentiate single-cell containing droplets, the cells were pre-stained with florescence dye. Within the same device, the single-cell containing droplets (Droplet B) were immediately sorted into the collection outlet by FADS (fluorescence-activated droplet sorting) and transferred to merging device via microbore tubing. The post-sorted droplets B occupied the rest space of microwells, forming pairs of A & B droplets. The droplet pairs will fuse to one droplet with an AC electrode field (FIG. 11c). The cell lysis took place in either droplet B or fused droplets depends on where the surfactant was present. After cells were lysed, we initiated RT-LAMP reactions at 62° C. (FIG. 11e). Six LAMP primers were used to target six regions of specific mRNA. If the target mRNA exists in the droplets (cells), the exponential amplification can be initiated and produced a great amount of DNA products in a very short time (10-20 min). The detection of LAMP reaction was based on the change of fluorescent intensity. FIG. 12 shows the fluorescence images before (FIG. 12a,b) and after (FIG. 12d,e,f) the single-cell RT-LAMP reaction. The increase of fluorescence signal is about 3.4 fold from purified DNA templates. The cell lysate shows a wider distribution of signal due to the cellular heterogeneity (FIG. 12c,e,f). The presence of precipitate LAMP products can also be confirmed by white light image (FIG. 12e). The single experiment can be finished in an hour with only 20 ul RT-LAMP reagent. We employed a design with 676 microwells in one device. The number of cells per experiment can be easily scaled up by changing the number of the microwells array or sequentially sorting droplets into multiple merging devices.

Performance of Single-Cell Capturing

To evaluate the performance of this droplet manipulation pipeline, we tested the efficiency of each step including droplet capturing, droplet pairing, single-cell isolation, and droplet merging (FIG. 13). The efficiency of each step is defined as the number of microwells contain desired droplets divided by total number of microwells in one device. At first step, the droplets with LAMP reactant were loaded and an average trapping efficiency of 99.6% was achieved. There was only occasional vacant wells due to the undesired capturing of dust or debris. At second step, the smaller droplet containing cells were loaded and an average pairing efficiency of 99.3% was achieved. The small decrease of the pairing efficiency was because of the error accumulation from repetition of droplet trapping. Among all the droplet pairs, 7% of them contain multiple cells, which is slightly higher than the estimated value of 4.9% predicted by Poisson distributions ($P_{Poisson,0.1}(x>1)/P_{Poisson,0.1}(x\geq1)=0.049$). We observed that higher number of doublet ratio were contributed by the clusters of cells due to unsuccessful dissociation. The chance of multiple cells in a droplet can be minimized by a higher dilution ratio of cell suspension or an improved preparation protocol for single-cell suspension. In conventional droplet merging approaches by either co-following or additive merging, the higher dilution indicates the higher reagent cost. In our method, the droplet with cells or reactant mixtures are generated separately, thus the only cost for a more diluted sample is the longer droplet sorting time. This can be compensated by a higher sorting throughput, as up to 30 kHz droplet sorting rate. Finally, the droplet pairs were merged by a short pulse of AC electrical field (800 Vp, 10 Khz, 0.5 s duration) across the entire droplet array. The average merging efficiency achieved >99% result in a final efficiency of 91.7% microwells containing LAMP reactant mixtures and a single-cell and 7% with multiple cells. The rest 1.3% microwells contained single droplet or unmerged droplet pairs. The failures of droplet merging was due to some outlier droplets with smaller size that cannot form physical contact with their adjacent droplets.

Optimization of RT-LAMP Reaction

Figure 14:
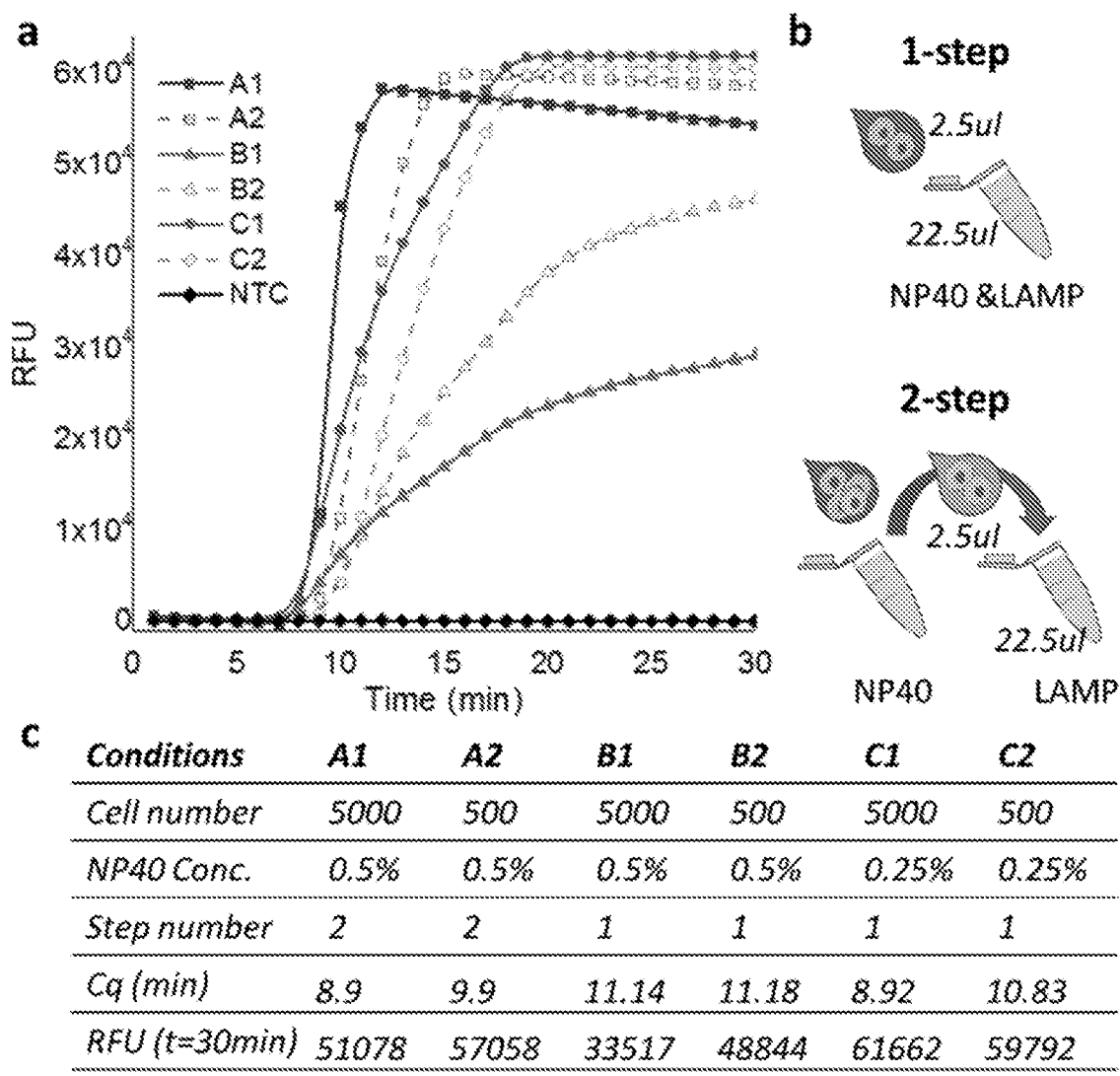
FIG. 14 shows a two-step lysis-amplification reaction for optimal RT-LAMP efficiency in Example 4. (a) Schematics of one-step and two-step RT-LAMP reaction protocols. In the one-step protocol, 2.5 uL of cell suspension (2E5 and 2E6 cells/mL) was added to 22.5 uL of RT-LAMP mix. In the two-step protocol, 50 uL of jurkat cell suspension (4E5 and 4E6 cells/mL) was first added to 50 uL of lysis buffer and then 2.5 uL of the lysed cell solution was added to 22.5 uL of RT-LAMP mix. The primer sets are designed to detect the sequence from HMBS gene. The cell and RT-LAMP mixes are then placed in a real-time PCR thermocycler and incubated at 62° C. for 30 minutes. (b) Representative results of real-time quantitative measurements under different conditions. (c) tables of different assay conditions. Cq is the critical time that reactions reach the exponential phase and RFU is the relative fluorescent intensity. Both Cq and RFU are directly measurement and determined by the real-time PCR thermocycler.

Although solubilising detergent Nonidet P-40 in lysis buffer has shown good combability to polymer chain reaction (PCR), there is no similar study for LAMP reaction. To optimize the concentration of NP-40 in LAMP assay, three conditions for the direct cell lysis and mRNA amplification by RT-qLAMP with limited jurkat cells (500 and 5,000 cells per 25 ul reactor) were tested using real-time PCR machine. FIG. 14 shows the real-time LAMP result of the different protocols (FIG. 14b,c). The LAMP reactant mixtures containing high concentration of (0.5%, protocol B) NP-40 showed more inhibitory effect to low concentration of NP-40 (0.25%, protocol C), which suggests that the lower concentration of NP-40 results in better activity of RT transcriptase or DNA polymerase. However, it is possible it may not have sufficient lysing effect if we further reduced the concentration of NP-40 since the typical concentration of NP-40 for lysing mammalian cells is about 0.5-1%. Therefore, we designed a two-step protocols by lysing cells in 0.5% NP-40 first and adding the cell lysate into the LAMP reactant mixtures at 1:10 dilution ratio (Protocol C). This maintained a higher concentration of NP-40 at lysis step but minimized its inhibitory effect for RT-LAMP reaction. The real-time RT-LAMP result also suggests that the two-step protocol has slightly better performance than 1-step protocol with low concentration of NP-40.

Comparison of Single-Cell and Bulk RT-LAMP Assay

To study the relation between the result of conventional bulk assay and our new droplet based single-cell assay, we scaled down the reactor volume of RT-LAMP assay from 25 microliter to 1.3 nanoliter. The number of cells per reactor was also reduced from about 500 to one cell and the number of reactors increased from one to 676. We observed the similar trend in single-cell assay that the two-step protocol has better sensitivity than both one-step protocols. Interestingly, we find a significant difference between two-step protocol and one-step protocol with 0.25% NP-40, but there is only a small difference between them in bulk assay. It can be explained by the different number of initial templates. In bulk assay, we have RNA templates from hundreds of cells and the LAMP reaction is so sensitive that only a few tens templates are required for initiating the chain reaction. Even the lysis or amplification condition are not optimal, it still has a great chance to initiate the amplification process. However, in single-cell assay, the initial templates are so rare. We could lose those precious and delicate mRNA templates during any step and results in the failures of the assay. Therefore, the two-step protocol is can be used to maximize the sensitivity of the reaction. To further characterize the detection limit for specific sequence or cell types, an RNA spike-in experiment could be performed.

Measurement of HMBS Gene Expression Across Various Cell Types

Figure 15:
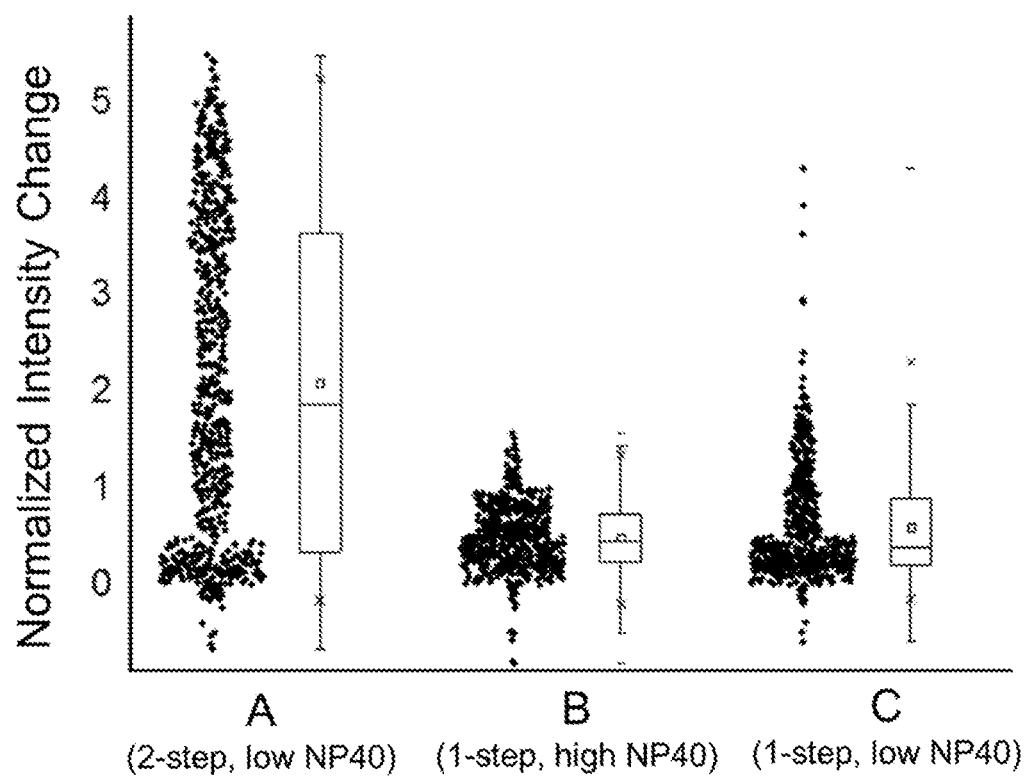
FIG. 15 shows a box plot of RT-LAMP results from Example 4 from three different protocols. Each dot represents a single-cell. The normalized intensity change is defined as $(I-I\_0)/I\_0$, where I is the end-point intensity and $I\_0$ is the initial intensity of each droplet. The experiment conditions are identical to FIG. 13 except the size of reactors reduce from 25 ul to 1.2 nL droplets.
Figure 16:
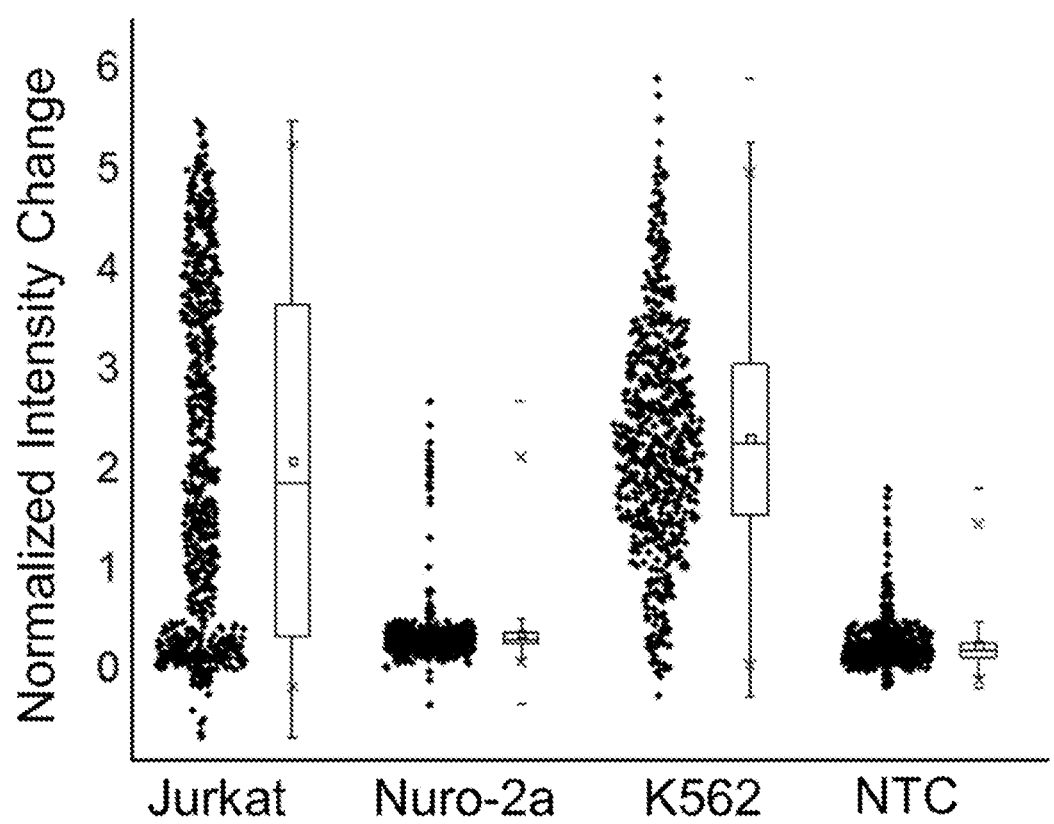
FIG. 16 shows a repetition of the experiment in FIG. 15 with Protocol A and other two cell lines (Nuro-2a and K562).

The HMBS gene expression of two human cell lines (Jurkat and K562) and a mouse cell line (Nuro-2A) were determined by using this system. About six hundred cells of each cell line and one background group (droplets contain only PBS buffer) were sorted into individual merging chips for RT-LAMP reaction. As described in the literature, as bone marrow tissue, K562 cells expressed a high level of HMBS protein and they are usually considered as the positive control for the detection of HMBS gene. On the other hand, Jurkat cells are considered to have medium HMBS expression level. FIG. 15 shows the quantification result of our sc-RT-LAMP assay. Both jurkat and K562 cells lines shows a higher population (62% and 96%, respectively) expressing HMBS gene than Nuro-2A and negative control (0.9% and 5%, respectively). The result agrees with our expectation since the primers were specifically designed for human hydroxymethylbilane synthase gene. Moreover, we observed a higher average signal from K562 than jurkat cells. This is also consistent with the result from our bulk measurement that the K562 cells shows a smaller Cq value than jurkat cells (supporting data).

By employing loop-mediated isothermal amplification in this platform, the target mRNA was spontaneously amplified within 30 minutes in the droplets with single-cell lysate, enabling rapid and high-specificity transcripts measurements. Three different samples: K562, jurkat, and Nuro-2 A cell lines were screened by using this platform. The human cells (K562 and jurkat) showing high HMBS expression levels were clearly distinguished from the mouse cells and negative control. Moreover, the K562 cells showed a higher HMBS expression level than the jurkat cells in statistical analysis, as expected.

REFERENCES

1. Mazutis et al., *Nat. Protoc.*, 2013, 8, 870-891.
2. Konry, et al., *Sci. Rep.*, 2013, 3, 3179.
3. Sjostrom, et al., *Lab Chip*, 2014, 14, 806-13.
4. Shembekar, et al., *Lab Chip*, 2016, 16, 1314-1331.
5. Rotem, *Nat. Biotechnol.*, 2015, 33, 1165-72.
6. Macosko et al., *Cell*, 2015, 161, 1202-1214.
7. Konry, et al., *Annu. Rev. Biomed. Eng.*, 2016, 18, 259-84.
8. Santesson et al., *Integr. Biol.* (*Camb*)., 2009, 1, 595-601.
9. Collins et al., *Lab Chip*, 2015, 3439-3459.
10. Sarkar et al., *J. Clin. Cell. Immunol.*, 2015, 6:3
11. Cao et al., *Lab chip*, 2013, 13, 171-178.
12. Hu et al., *Lab Chip*, 2015, 15, 3989-3993.
13. Edd et al., *Lab chip*, 2008, 8, 1262-1264.
14. Lagus and Edd, *RSC Adv.*, 2013, 3, 20512.
15. Abate et al., *Lab Chip*, 2009, 9, 2628-2631.
16. Klein et al., *Cell*, 2015, 161, 1187-1201.
17. Lee et al., *Lab Chip*, 2014, 14, 509-13.
18. Lee et al., *Microfluid. Nanofluidics*, 2016, 20, 1-9.
19. Fradet et al., *Lab Chip*, 2011, 11, 4228.
20. Baret et al., *Lab Chip*, 2009, 9, 1850-8.
21. Hong et al., *Integr. Biol.*, 2012, 4, 374.
22. Anna et al., *Appl. Phys. Lett.*, 2003, 82, 364-366.
23. Baroud et al., *Lab chip*, 2010, 10, 2032.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
   a) a plurality of first droplets and a plurality of second droplets, wherein said second droplets are smaller than said first droplets;
   b) a substrate comprising a plurality of trapping sites, wherein each of said trapping sites is configured to trap one and only one of said first droplets, and wherein each of said trapping sites is further configured to trap one and only one of said second droplets when a first droplet is present in said trapping site.

2. A method comprising:
   a) dispensing a plurality of first droplets into a flow cell containing a substrate which comprises a plurality of trapping sites such that one and only one of said first droplets is captured in each of said trapping sites; and
   b) dispensing a plurality of second droplets into said flow cell such that one and only one of said second droplets is captured in each of said trapping sites that contains one of said first droplets, wherein said second droplets are smaller than said first droplets.

3. The method of claim 2, wherein any excess first droplets are flushed away from said substrate with a fluid after step a) but before step b).

4. The method of claim 2, wherein any excess second droplets are flushed away from said substrate with a fluid after step b).

5. The method of claim 2, further comprising: c) treating said substrate such that said first and second droplets at each of said trapping sites merge into a single merged droplet, thereby generating a plurality of merged droplets.

6. The method of claim 5, wherein said treating comprises dispensing a demulsifier into said flow cell.

7. The method of claim 5, wherein said treating comprises providing said substrate with electricity.

8. The method of claim 7, wherein said substrate comprises an embedded wire, and wherein said providing said substrate with electricity comprises sending an electric current through said embedded wire.

9. The method of claim 5, further comprising d) dispensing a liquid comprising a surfactant into said flow cell such that said surfactant stabilizes said merged droplets.

10. The method of claim 5, further comprising: d) collecting said merged droplets from said flow cell into a container.

11. The method of claim 10, wherein said collecting comprises inverting said substrate such that said plurality of merged droplets float out of said plurality of trapping sites and are flowed out of said flow cell into said container.

12. The method of claim 5, further comprising: d) dispensing amplification reagents into said trapping sites.

13. The method of claim 12, further comprising: e) treating said merged droplets at said trapping sites under conditions such that a sequencing library of sequencing templates is generated via an amplification reaction.

14. The method of claim 13, wherein each of said sequencing templates comprises: i) first and second barcode sequences, or complements thereof, and ii) a nucleic acid sequence of a coding region from an mRNA sequence, or complement thereof.

15. The method of claim 13, further comprising: f) sequencing at least a portion of said sequencing library.

16. The method of claim 2, wherein said plurality of first droplets and/or said plurality of second droplets, each contain one, and only one, cell.

17. The method of claim 2, wherein said plurality of first droplets and/or said plurality of second droplets, each contain one, and only one, bead and/or type of nucleic acid barcode.

18. The method of claim 2, wherein said plurality of first droplets each contain one, and only one, bead, and wherein said plurality of second droplets each contain one, and only one, cell.

19. The method of claim 2, wherein said plurality of first droplets and/or said plurality of second droplets each comprise water-in-oil droplets.

20. An article of manufacture comprising a substrate, wherein said substrate comprises a plurality of trapping sites,
   wherein each of said trapping sites is configured to trap one and only one of a first-sized droplet,
   wherein each of said trapping sites is further configured to trap one and only one of a second-sized droplet when a first-sized droplet is present in said trapping site, and
   wherein said second-sized droplet is smaller than said first-sized droplet.

* * * * *